(12) United States Patent
Sutherland et al.

(10) Patent No.: US 10,098,973 B2
(45) Date of Patent: Oct. 16, 2018

(54) ANTI-TAU ANTIBODY AND USES THEREOF

(71) Applicant: National Research Council of Canada, Ottawa (CA)

(72) Inventors: Garnette R. Sutherland, Calgary (CA); Sanju Lama, Calgary (CA); Mehdi Arbabi-Ghahroudi, Ottawa (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 15/518,069

(22) PCT Filed: Oct. 6, 2015

(86) PCT No.: PCT/IB2015/057645
§ 371 (c)(1),
(2) Date: Apr. 10, 2017

(87) PCT Pub. No.: WO2016/055941
PCT Pub. Date: Apr. 14, 2016

(65) Prior Publication Data
US 2017/0296680 A1 Oct. 19, 2017

Related U.S. Application Data

(60) Provisional application No. 62/173,452, filed on Jun. 10, 2015, provisional application No. 62/062,417, filed on Oct. 10, 2014.

(51) Int. Cl.
| | |
|---|---|
| *A61K 49/18* | (2006.01) |
| *A61K 51/12* | (2006.01) |
| *C07K 16/18* | (2006.01) |
| *C07K 17/14* | (2006.01) |
| *C07K 17/00* | (2006.01) |
| *G01N 33/53* | (2006.01) |
| *G01N 33/00* | (2006.01) |
| *G01N 33/567* | (2006.01) |

(52) U.S. Cl.
CPC .......... *A61K 49/1875* (2013.01); *A61K 51/12* (2013.01); *C07K 16/18* (2013.01); *C07K 17/14* (2013.01); *G01N 33/53* (2013.01); *G01N 33/567* (2013.01); *C07K 17/00* (2013.01); *G01N 33/00* (2013.01)

(58) Field of Classification Search
None
See application file for complete search history.

(56) References Cited

U.S. PATENT DOCUMENTS

| | | |
|---|---|---|
| 5,693,761 A | 12/1997 | Queen et al. |
| 5,766,886 A | 6/1998 | Studnicka et al. |
| 5,821,123 A | 10/1998 | Studnicka |
| 5,859,205 A | 1/1999 | Adair et al. |
| 5,869,619 A | 2/1999 | Studnicka |
| 6,054,297 A | 4/2000 | Carter et al. |
| 6,180,370 B1 | 1/2001 | Queen et al. |

FOREIGN PATENT DOCUMENTS

| | | |
|---|---|---|
| EP | 0 519 596 A1 | 12/1992 |
| EP | 0 626 390 A1 | 11/1994 |
| WO | WO 1995/004069 A1 | 2/1995 |
| WO | WO 2003/046560 A2 | 6/2003 |
| WO | WO 2004/076670 A1 | 9/2004 |
| WO | WO 2013/007839 A1 | 1/2013 |

OTHER PUBLICATIONS

Chen "enhancement and destruction of antibody function by somatic mutation: unequal occurrence is controlled by V gene combinatorial associations" EMBO 14(12):2784-2794 (Year: 1995).*
Arbabi Ghahroudi et al., Selection and identification of single domain antibody fragments from camel heavy-chain antibodies. FEBS Lett. Sep. 15, 1997;414(3):521-6.
Arbabi-Ghahroudi et al., Selection of non-aggregating VH binders from synthetic VH phage-display libraries. Methods Mol Biol. 2009;525:187-216, xiii. doi: 10.1007/978-1-59745-554-1_10.
Avila et al., Tau in neurodegenerative diseases: tau phosphorylation and assembly. Neurotox Res. 2004;6(6):477-82.
Ballatore et al., Tau-mediated neurodegeneration in Alzheimer's disease and related disorders. Nat Rev Neurosci. Sep. 2007;8(9):663-72.
Baral et al., Single-domain antibodies and their utility. Curr Protoc Immunol. Nov. 18, 2013;103:Unit 2.17 . . . doi:10.1002/0471142735. im0217s103.
Bell et al., Differential tumor-targeting abilities of three single-domain antibody formats. Cancer Lett. Mar. 1, 2010;289(1):81-90. doi: 10.1016/j.canlet.2009.08.003. Epub Aug. 28, 2009.
Bigler et al., Neuropathology of mild traumatic brain injury: relationship to neuroimaging findings. Brain Imaging Behav. Jun. 2012;6(2):108-36. doi: 10.1007/s11682-011-9145-0.
Chothia et al., Canonical structures for the hypervariable regions of immunoglobulins. J Mol Biol. Aug. 20, 1987;196(4):901-17.
Corrigan et al., The epidemiology of traumatic brain injury. J Head Trauma Rehabil. Mar.-Apr. 2010;25(2):72-80. doi:10.1097/HTR. 0b013e3181ccc8b4. Review. Erratum in: J Head Trauma Rehabil. May-Jun. 2010;25(3):224.
Das et al., NaDyF4 nanoparticles as T2 contrast agents for ultrahigh field magnetic resonance imaging. J Phys Chem Lett. Feb. 16, 2012;3(4):524-9. doi: 10.1021/jz201664h. Epub Feb. 7, 2012.
David et al., Potential candidate camelid antibodies for the treatment of protein-misfolding diseases. J Neuroimmunol. Jul. 15, 2014;272(1-2):76-85. doi: 10.1016/j.jneuroim.2014.05.001. Epub May 10, 2014.
Davies et al., Affinity improvement of single antibody VH domains: residues in all three hypervariable regions affect antigen binding. Immunotechnology. Sep. 1996;2(3):169-79.
De Kruif et al., Leucine zipper dimerized bivalent and bispecific scFv antibodies from a semi-synthetic antibody phage display library. J Biol Chem. Mar. 29, 1996;271(13):7630-4.

(Continued)

*Primary Examiner* — Adam M Weidner
(74) *Attorney, Agent, or Firm* — Wolf, Greenfield & Sacks, P.C.

(57) ABSTRACT

The present invention relates to Tau-specific antibodies, fragments thereof, and uses thereof. More specifically, the present invention relates to Tau-specific antibodies, fragments thereof, and conjugates thereof with conjugated to a superparamagnetic nanoparticle. The molecules of the present invention may be used in visualizing damage from traumatic brain injury.

20 Claims, 14 Drawing Sheets

Specification includes a Sequence Listing.

(56) References Cited

OTHER PUBLICATIONS

Dekosky et al., Traumatic brain injury—football, warfare, and long-term effects. N Engl J Med. Sep. 30, 2010;363(14):1293-6. doi:10.1056/NEJMp1007051. Epub Sep. 22, 2010.
Dumoulin et al., Single-domain antibody fragments with high conformational stability. Protein Sci. Mar. 2002;11(3):500-15.
Durocher et al., High-level and high-throughput recombinant protein production by transient transfection of suspension-growing human 293-EBNA1 cells. Nucleic Acids Res. Jan. 15, 2002;30(2):e9.
Eierud et al., Neuroimaging after mild traumatic brain injury: review and meta-analysis. Neuroimage Clin. Jan. 4, 2014;4:283-94. doi: 10.1016/j.nicl.2013.12.009. eCollection 2014.
Eisenberg et al., Analysis of membrane and surface protein sequences with the hydrophobic moment plot. J Mol Biol. Oct. 15, 1984;179(1):125-42.
Fenner et al., Rapid and reliable diagnostic algorithm for detection of Clostridium difficile. J Clin Microbiol. Jan. 2008;46(1):328-30. Epub Nov. 21, 2007.
Fodero-Tavoletti et al., 18F-THK523: a novel in vivo tau imaging ligand for Alzheimer's disease. Brain. Apr. 2011;134(Pt 4):1089-100. doi: 10.1093/brain/awr038. Epub Mar. 24, 2011.
Goda et al., Photoconductive stimulation of neurons cultured on silicon wafers. Nat Protoc. 2006;1(1):461-7.
Goldstein et al., Chronic traumatic encephalopathy in blast-exposed military veterans and a blast neurotrauma mouse model. Sci Transl Med. May 16, 2012;4(134):134ra60. doi: 10.1126/scitranslmed. 3003716.
Grundke-Iqbal et al., Microtubule-associated protein tau. A component of Alzheimer paired helical filaments. J Biol Chem. May 5, 1986;261(13):6084-9.
Grundke-Iqbal et al., Abnormal phosphorylation of the microtubule-associated protein tau (tau) in Alzheimer cytoskeletal pathology. Proc Natl Acad Sci U S A. Jul. 1986;83(13):4913-7.
Hamers-Casterman et al., Naturally occurring antibodies devoid of light chains. Nature. Jun. 3, 1993;363(6428):446-8.
Hirokawa et al., Selective stabilization of tau in axons and microtubule-associated protein 2C in cell bodies and dendrites contributes to polarized localization of cytoskeletal proteins in mature neurons. J Cell Biol. Feb. 1996;132(4):667-79.
Hussack et al., Engineered single-domain antibodies with high protease resistance and thermal stability. PLoS One. 2011;6(11):e28218. doi: 10.1371/journal.pone.0028218. Epub Nov. 30, 2011.
Iqbal et al., Kinetic analysis of novel mono- and multivalent VHH-fragments and their application for molecular imaging of brain tumours. Br J Pharmacol. Jun. 2010;160(4):1016-28. doi:10. 1111/j.1476-5381.2010.00742.x.
Jaffee et al., A brief overview of traumatic brain injury (TBI) and post-traumatic stress disorder (PTSD) within the Department of Defense. Clin Neuropsychol. Nov. 2009;23(8):1291-8. doi: 10.1080/ 13854040903307250.
Jeganathan et al., The natively unfolded character of tau and its aggregation to Alzheimer-like paired helical filaments. Biochemistry. Oct. 7, 2008;47(40):10526-39. doi: 10.1021/bi800783d. Epub Sep. 11, 2008.
Jespers et al., Aggregation-resistant domain antibodies selected on phage by heat denaturation. Nat Biotechnol. Sep. 2004;22(9):1161-5. Epub Aug. 8, 2004.
Johnson et al., Self-focusing by Ostwald ripening: a strategy for layer-by-layer epitaxial growth on upconverting nanocrystals. J Am Chem Soc. Jul. 11, 2012;134(27):11068-71. doi: 10.1021/ ja302717u. Epub Jun. 26, 2012.
Johnson et al., Traumatic brain injury and amyloid-β pathology: a link to Alzheimer's disease? Nat Rev Neurosci. May 2010;11(5):361-70. doi: 10.1038/nrn2808.
Kabat et al., Identical V region amino acid sequences and segments of sequences in antibodies of different specificities. Relative contributions of VH and VL genes, minigenes, and complementarity-determining regions to binding of antibody-combining sites. J Immunol. Sep. 1, 1991;147(5):1709-19.

Kane et al., A mouse model of human repetitive mild traumatic brain injury. J Neurosci Methods. Jan. 15, 2012;203(1):41-9. doi: 10.1016/ j.jneumeth.2011.09.003. Epub Sep. 12, 2011.
Kim et al., Disulfide linkage engineering for improving biophysical properties of human VH domains. Protein Eng Des Sel. Oct. 2012;25(10):581-9. Epub Aug. 30, 2012.
Klimo et al., Introduction: military neurosurgery, past and present. Neurosurg Focus. May 2010;28(5):1-2.
Lafaye et al., Anti-Ab and anti-tau camel single-domain antibodies: a new tool for in vivo imaging and potential diagnosis of Alzheimer's Disease. Alzheimer's & Dementia: The Journal of the Alzheimer's Association . Jul. 2014;10(4):P252.
Lama et al., Lactate storm marks cerebral metabolism following brain trauma. J Biol Chem. Jul. 18, 2014;289(29):20200-8. doi: 10.1074/jbc.M114.570978. Epub May 21, 2014.
Lefranc et al., IMGT unique numbering for immunoglobulin and T cell receptor variable domains and Ig superfamily V-like domains. Dev Comp Immunol. Jan. 2003;27(1):55-77.
Li et al., Pentabody-mediated antigen delivery induces antigen-specific mucosal immune response. Mol Immunol. May 2009;46(8-9):1718-26. doi:10.1016/j.molimm.2009.02.007. Epub Mar. 9, 2009.
Marshall et al., Clinical practice guidelines for mild traumatic brain injury and persistent symptoms. Can Fam Physician. Mar. 2012;58(3):257-67, e128-40.
McKee et al., Chronic traumatic encephalopathy in athletes: progressive tauopathy after repetitive head injury. J Neuropathol Exp Neurol. Jul. 2009;68(7):709-35. doi: 10.1097/NEN.0b013e3181a9d503.
Merritt et al., AB5 toxins. Curr Opin Struct Biol. Apr. 1995;S(2):165-71.
Musher et al., Detection of Clostridium difficile toxin: comparison of enzyme immunoassay results with results obtained by cytotoxicity assay. J Clin Microbiol. Aug. 2007;45(8):2737-9. Epub Jun. 13, 2007.
Neely et al., Ultrasensitive and highly selective detection of Alzheimer's disease biomarker using two-photon Rayleigh scattering properties of gold nanoparticle. ACS Nano. Sep. 22, 2009;3(9):2834-40. doi: 10.1021/nn900813b.
Nicaise et al., Affinity transfer by CDR grafting on a nonimmunoglobulin scaffold. Protein Sci. Jul. 2004;13(7):1882-91. Epub May 28, 2004.
Nuttall et al. Isolation and characterization of an IgNAR variable domain specific for the human mitochondrial translocase receptor Tom70. Eur J Biochem. Sep. 2003;270(17):3543-54.
Pace et al., How to determine the molar absorbance coefficient of a protein. Protein Structure: A Practical Approach. pp. 253-259 (1997).
Park et al., Traumatic brain injury: can the consequences be stopped? CMAJ. Apr. 22, 2008;178(9):1163-70. doi: 10.1503/cmaj.080282.
Pickett et al., A population-based study of potential brain injuries requiring emergency care. CMAJ. Aug. 7, 2001;165(3):288-92.
Planche et al., Diagnosis of Clostridium difficile infection by toxin detection kits: a systematic review. Lancet Infect Dis. Dec. 2008;8(12):777-84. doi: 10.1016/S1473-3099(08)70233-0. Epub Nov. 1, 2008.
Rüssmann et al., Evaluation of three rapid assays for detection of Clostridium difficile toxin A and toxin B in stool specimens. Eur J Clin Microbiol Infect Dis. Feb. 2007;26(2):115-9.
Selenica et al., Epitope analysis following active immunization with tau proteins reveals immunogens implicated in tau pathogenesis. J Neuroinflammation. Sep. 3, 2014;11:152. doi: 10.1186/s12974-014-0152-0.
Tanha et al., Selection by phage display of llama conventional V(H) fragments with heavy chain antibody V(H)H properties. J Immunol Methods. May 1, 2002;263(1-2):97-109.
To et al., Isolation of monomeric human V(H)s by a phage selection. J Biol Chem. Dec. 16, 2005;280(50):41395-403. Epub Oct. 12, 2005.
Tom et al., Culture of HEK293-EBNA1 Cells for Production of Recombinant Proteins. CSH Protoc. Mar. 1, 2008;2008:pdb. prot4976. doi:10.1101/pdb.prot4976.
Turgeon et al., Six rapid tests for direct detection of Clostridium difficile and its toxins in fecal samples compared with the fibroblast cytotoxicity assay. J Clin Microbiol. Feb. 2003;41(2):667-70.

(56) References Cited

OTHER PUBLICATIONS

Vagnozzi et al., Hypothesis of the postconcussive vulnerable brain: experimental evidence of its metabolic occurrence. Neurosurgery. Jul. 2005;57(1):164-71; discussion 164-71.

Vagnozzi et al., Temporal window of metabolic brain vulnerability to concussions: mitochondrial-related impairment—part I. Neurosurgery. Aug. 2007;61(2):379-88; discussion 388-9.

Van Den Heuvel et al., Traumatic brain injury and Alzheimer's disease: a review. Prog Brain Res. 2007;161:303-16.

Weber, Experimental models of repetitive brain injuries. Prog Brain Res. 2007;161:253-61.

Zetterberg et al., Biomarkers of mild traumatic brain injury in cerebrospinal fluid and blood. Nat Rev Neurol. Apr. 2013;9(4):201-10. doi:10.1038/nrneurol.2013.9. Epub Feb. 12, 2013.

Zhang et al., A pentavalent single-domain antibody approach to tumor antigen discovery and the development of novel proteomics reagents. J Mol Biol. Jul. 30, 2004;341(1):161-9.

Zhang et al., Pentamerization of single-domain antibodies from phage libraries: a novel strategy for the rapid generation of high-avidity antibody reagents. J Mol Biol. Jan. 2, 2004;335(1):49-56.

Zhu et al., Combody: one-domain antibody multimer with improved avidity. Immunol Cell Biol. Aug. 2010;88(6):667-75. doi: 10.1038/icb.2010.21. Epub Mar. 9, 2010.

\* cited by examiner

ANTI-TAU ANTIBODY AND USES THEREOF

RELATED APPLICATIONS

This application is a national stage filing under 35 U.S.C. § 371 of International Application No. PCT/IB2015/057645, filed Oct. 6, 2015, which was published under PCT Article 21(2) in English, and claims the benefit under 35 U.S.C. § 119(e) of U.S. Provisional Patent Application Ser. No. 62/062,417, filed Oct. 10, 2014 and U.S. Provisional Patent Application Ser. No. 62/173,452, filed Jun. 10, 2015, the entire contents of each of which is incorporated herein by reference in its entirety.

FIELD OF THE INVENTION

The present invention relates to Tau-specific antibodies, fragments thereof, and uses thereof. More specifically, the present invention relates to Tau-specific antibodies, fragments thereof, and uses thereof in visualizing damage from traumatic brain injury.

BACKGROUND OF THE INVENTION

Tau is an intracellular microtubule-associated protein that regulates microtubule dynamics, axonal transport, and neurite outgrowth. Tau promotes microtubule assembly and is believed to be responsible for establishing neuronal polarity (Avila et al, 2004; Hirokawa et al, 1996). A natively unfolded protein, the C-terminus of the tau binds to the axonal microtubules while the N-terminus binds to the neural plasma membrane. The functions of tau are modulated via sit-specific phosphorylation. While phosphorylation is necessary for functional regulation, abnormal and excessive phosphorylation, observed in pathological states such as Alzheimer's disease and TBI, renders the protein non-functional, thus disrupting micro-tubular structure and cell death.

Alzheimer's disease (AD) is an age-dependent dementia. It has been shown that abnormally hyper-phosphorylated tau is the major protein subunit of paired helical filaments (PHF) that form intracellular neurofibrillary tangles in the brain of AD patients (Grundke-lqbal, 1986a and 1986b). The deposition of hyper-phosphorylated tau is generally localized to the temporal lobe in AD.

Traumatic brain injury may be classified into two components: i) primary brain injury occurring as a result of direct impact, and ii) secondary brain injury associated with the molecular and cellular response to injury that follows primary impact (Park et al, 2008). Recently, abnormal deposition of tau was observed in in post-mortem brains obtained from patients who suffered repetitive mild TBI during their lifetime (McKee et al, 2009; Goldstein et al, 2012). More specifically, the hyper-phosphorylated tau accumulates in neurofibrillary tangles (DeKosky et al, 2010) in the deep sulci and gyri, amygdala, and hippocampi. Hyper-phosphorylated tau has been observed both intracellular and extracellular locations in traumatic brain injury.

In Canada approximately 18,000 people per annum suffer traumatic brain injury (TBI), representing 12% of all injury hospitalizations. Most of these patients (65%) are young adults, and the direct plus indirect costs to society are estimated at approximately $1 billion (Pickett et al, 2001; Corrigan et al, 2010). Growing incidence of military combat- and sports-related repetitive mild injury to the brain emphasize not only the importance of prevention and acute treatment but also the increasing need for methods that provide an assessment of disease extent and its long term neurological sequel (Jaffee & Meyer, 2009; Klimo & Ragel, 2010; DeKosky & Ikonomovic, 2010). Although termed concussion or mild TBI, the many diverse and often disabling effects render the affected individuals unable to function at normal capacity. It is important not only to establish that TBI has occurred, but also objectively quantify the extent of damage in order to provide timely patient specific care.

Hyper-phosphorylation of tau relates to the characteristic cognitive impairment in both AD and TBI. Indeed, many studies suggest a link between TBI and a higher risk of later developing AD (Van Den Heuvel et al, 2007). While there have been reports on long term predictors of moderate and severe TBI relative to neurological function and recovery, more sensitive, specific and non-invasive methods of assessment are needed, specifically for mild TBI (Bigler & Maxwell, 2012; Marshall et al, 2012). This is particularly highlighted by the fact that, in the absence of definitive imaging techniques, diagnosis largely relies on a range of symptom complex.

In mild TBI, there presently exists a dissociation between neurological impairment and MR imaging, i.e. significant symptoms with relatively normal MR imaging (Eierud et al, 2014). While serum and cerebrospinal fluid biomarkers for TBI have evolved, with a few being studied for mild injury, there is presently no definitive imaging biomarker for mild TBI (Zetterburg, 2013). Based on the above-mentioned pathological studies, tau or its hyper-phosphorylated form could well represent a target for biomarker development.

Emerging techniques in cellular imaging have shown some progress in the use of monoclonal anti-tau antibody-coated gold nanoparticle based assays for ligand-based visualization of tau in vitro (Neely et al, 2009) and ligand-based radio-active tracers for in vivo visualization of tau in tau transgenic mice brains (Fodero-Tavoletti et al, 2011), in the context of Alzheimer's disease research.

However, generating antibodies against tau remains a challenge for the following reasons. First, tau is in a natively unfolded conformation state (Jeganathan et al, 2008). Second, it is poorly immunogenic most likely due to the fact that it has a highly conserved self-antigenic nature. While high-affinity monoclonal antibodies against tau have been generated in tau-knockout mice (Selenica et al, 2014), these have limited applications due to their large size in crossing the neuronal barriers or safety concerns for in vivo use.

The lack of specific and safe targeting agents for imaging of TBI as well as AD is an obstacle in early diagnosis. As a result, there is no mechanism in the art to visualize tau abnormality using magnetic resonance (MR) imaging.

SUMMARY OF THE INVENTION

The present invention relates to Tau-specific antibodies, fragments thereof, and uses thereof. More specifically, the present invention relates to Tau-specific antibodies, fragments thereof, and uses thereof in visualizing damage from traumatic brain injury.

The present invention further provides an isolated or purified antibody or fragment thereof, comprising
- a complementarity determining region (CDR) 1 sequence of GFTFSNFA (SEQ ID NO:1) or GFTGDHYA (SEQ ID NO:4);
- a CDR2 sequence of IDNDGGRT (SEQ ID NO:2) or IYSYSPNT (SEQ ID NO:5);
- a CDR3 sequence of AAMNLATRKWEL (SEQ ID NO:3) or AADLEVAEYYAY (SEQ ID NO:6); and valine at position 42, glycine at position 49, leucine at position 50, and tryptophan at position 52 of the framework (IMGT numbering),
wherein the antibody or fragment thereof specifically binds to Tau.

For example, and without wishing to be limiting in any manner, the isolated or purified antibody or fragment thereof may comprise
a CDR1 sequence of GFTFSNFA (SEQ ID NO:1), a CDR2 sequence of IDNDGGRT (SEQ ID NO:2), and a CDR3 sequence of AAMNLATRKWEL (SEQ ID NO:3); or
a CDR1 sequence of GFTGDHYA (SEQ ID NO:4), a CDR2 sequence of IYSYSPNT (SEQ ID NO:5), and a CDR3 sequence of AADLEVAEYYAY (SEQ ID NO:6).

In a more specific, non-limiting example, the isolated antibody or fragment thereof may comprise a sequence selected from the group consisting of:

```
          (SEQ ID NO: 7, referred to herein as Tau15)
QVKLEESGGGLVQPGGSLRLSCAASGFTFSNFAMTWVRQSPGKGLEWVS

AIDNDGGRTSYSDSVKGRFTISRDNAKNTLYLQMNSLKPEDTAMYYCAA

MNLATRKWELWGQGTQVTVSS;

(SEQ ID NO: 8, referred to herein as Tau81)
QVQLVESGGGLVQPGGSLKLSCAASGFTGDHYAMSWVRQAPGKGLEWVS

TIYSYSPNTYYVDSVKDRFTISLDNAKNTLYLQMNSLKPEDTAVYYCAA

DLEVAEYYAYWGQGTQVTVSS;
``` and
a sequence substantially identical thereto.

The isolated or purified antibody or fragment thereof as described above may be a single-domain antibody (sdAb); the sdAb may be of camelid origin.

The isolated or purified antibody or fragment thereof of the present invention may be presented in a multivalent display format. In a multivalent display format, the antibody or fragment thereof may be linked to a Fc or fragment thereof, for example a Fc, $C_{H1}$ domain, $C_{H2}$ domain, $C_{H3}$ domain, the hinge region, or any combination thereof. In one example, the Fc or fragment thereof may be the mouse Fc gamma 2b or human Fc gamma1. In an alternative example, the Fc or fragment thereof may be the human hinge region sequence AEPISCDKTHTCPPCP (SEQ ID NO:16) or ETSSPAEPKSCDKTHTCPPCP (SEQ ID NO:17).

The present invention also provides a nucleic acid molecule encoding the isolated or purified antibody or fragment thereof as described herein. A vector comprising the nucleic acid molecule as just described is also provided.

The isolated or purified antibody or fragment thereof as described herein may be immobilized onto a surface.

The present invention further provides the isolated or purified antibody or fragment thereof as described herein linked to a cargo molecule. The cargo molecule may be a detectable agent, a therapeutic, a drug, a peptide, a growth factor, a cytokine, a receptor trap, a chemical compound, a carbohydrate moiety, an enzyme, an antibody or fragments thereof, a DNA-based molecule, a viral vector, or a cytotoxic agent; one or more liposomes or nanocarriers loaded with a detectable agent, a therapeutic, a drug, a peptide, an enzyme, and antibody or fragments thereof, a DNA-based molecule, a viral vector, or a cytotoxic agent; or one or more nanoparticle, nanowire, nanotube, or quantum dots.

In one example, the cargo molecule may be a detectable agent, or a liposomes or nanocarriers loaded with a detectable agent. In a specific, non-limiting example, the detectable label may be a superparamagnetic nanoparticle. The nanoparticle may be a NaDyF4-NaGdF4 core-shell nanoparticle, a silica-coated ferrous oxide, gold nanoparticle, β-NaYF$_4$:Yb,Gd,Tm, gadolinium nanoparticle, or a solid lipid nanoparticles. Such nanoparticles may have a size of about 10 to about 50 nm. The nanoparticles may have about 4 to about 22 antibodies or fragment thereof conjugated to the surface of the nanoparticle. In specific example, there may be about 4, 12, or 22 conjugated to the surface of the nanoparticle.

Additionally, the present invention also provides a composition comprising one or more than one isolated or purified antibody or fragment thereof as described herein and a pharmaceutically-acceptable carrier, diluent, or excipient.

The present invention further provides and in vitro method of detecting tau, comprising
a) contacting a tissue sample with one or more than one isolated or purified antibody or fragment thereof as described herein linked to a detectable agent; and
b) detecting the detectable agent linked to the antibody or fragment thereof bound to tau in the tissue sample.

In the above method, the tissue sample may be a brain tissue sample from a human or animal subject. The step of detecting (step b) may be performed using optical imaging, immunohistochemistry, molecular diagnostic imaging, ELISA, imaging mass spectrometry, or any other suitable method known in the art.

The present invention also provides an in vivo method of detecting tau expression in a subject, comprising:
a) administering one or more than one isolated or purified antibody or fragment thereof described herein linked to a detectable agent to the subject; and
b) detecting the detectable agent linked to the antibody or fragment thereof bound to tau.

In the above in vivo method, the step of detecting (step b) may be performed using magnetic resonance imaging (MRI). The detectable label used in the above method may be a superparamagnetic nanoparticle; in a more specific example, the nanoparticle may be a NaDyF4-NaGdF4 core-shell nanoparticle. The nanoparticle may have a size of about 10 to about 50 nm; there may be about 4, 12, or 22 antibodies or fragment thereof conjugated to the surface of the nanoparticle. In one example the antibody or fragment thereof may be Tau15.

Additional aspects and advantages of the present invention will be apparent in view of the following description. The detailed descriptions and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 2 shows the analysis of protein purity for selected anti-Tau sdAb phage clones.

FIG. 10A shows results of a 1:100 dilution of anti-tau sdAb-NaDyF4-NaGdF4-Alexa488, while FIG. 10B shows results of a 1:200 dilution of rabbit anti-tau commercial antibody with 1:2000 cy3 secondary antibody. FIG. 10C shows an overlay of FIGS. 10A and 10B, demonstrating that neuronal tau protein is targeted by both the anti-tau sdAb-NaDyF4-NaGdF4-Alexa488 and the rabbit anti-tau commercial antibody. Neither antibody stained glial cells present in the culture.

FIG. 12A shows that a 1:20 dilution of anti-tau sdAb-NaDyF4-NaGdF4-Alexa488 labelled neuronal tau protein (40× magnification). FIG. 12B shows labelling with a 1:10 dilution of NaDyF4-NaGdF4-Alexa488 only (20× magnification).

DETAILED DESCRIPTION OF THE INVENTION

Figure 1:
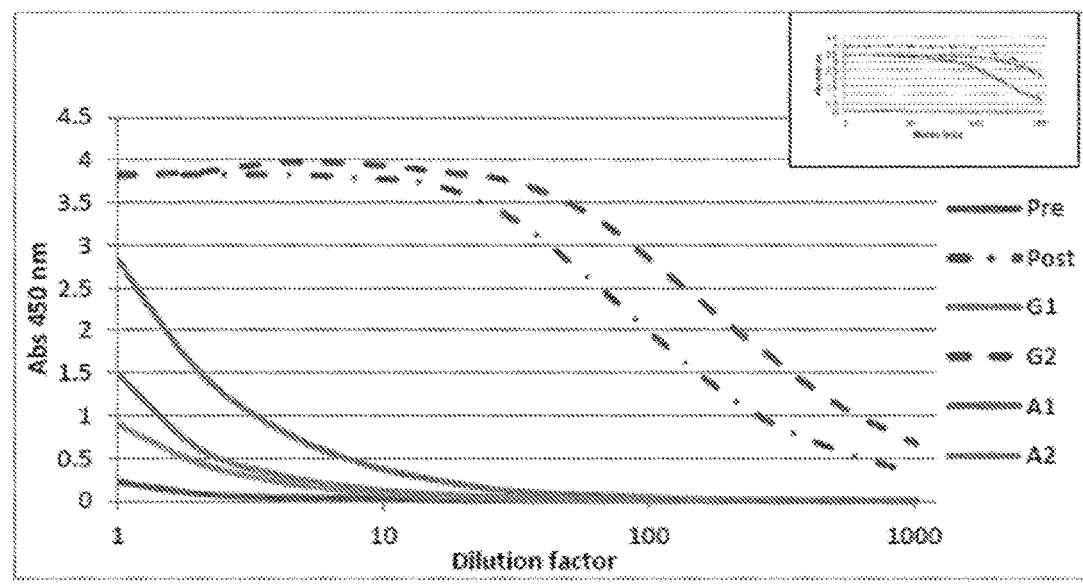
FIG. 1 shows the total, conventional, and heavy chain antibody responses against tau. As shown, total and conventional fraction (G2) immune responses against tau are quite strong. However, there is a rather weak heavy chain response (G1, A1 and A2) compared to the pre-immune serum.

The present invention relates to Tau-specific antibodies, fragments thereof, and uses thereof. More specifically, the present invention relates to Tau-specific antibodies, fragments thereof, and uses thereof in visualizing damage from traumatic brain injury.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The present invention further provides an isolated or purified antibody or fragment thereof, comprising
  a complementarity determining region (CDR) 1 sequence of GFTFSNFA (SEQ ID NO:1) or GFTGDHYA (SEQ ID NO:4);
  a CDR2 sequence of IDNDGGRT (SEQ ID NO:2) or IYSYSPNT (SEQ ID NO:5);
  a CDR3 sequence of AAMNLATRKWEL (SEQ ID NO:3) or AADLEVAEYYAY (SEQ ID NO:6); and
  valine at position 42, glycine at position 49, leucine at position 50, and tryptophan at position 52 of the framework (IMGT numbering),
wherein the antibody or fragment thereof specifically binds to Tau.

The term "antibody", also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. These individual schemes define CDR and hypervariable loop regions that are adjacent or overlapping, those of skill in the antibody art often utilize the terms "CDR" and "hypervariable loop" interchangeably, and they may be so used herein. The CDR/loops are referred to herein according to the more recent IMGT numbering system (Lefranc, M.-P. et al., 2003), which was developed to facilitate comparison of variable domains. In this system, conserved amino acids (such as Cys23, Trp41, Cys104, Phe/Trp118, and a hydrophobic residue at position 89) always have the same position. Additionally, a standardized delimitation of the framework regions (FR1: positions 1 to 26; FR2: 39 to 55; FR3: 66 to 104; and FR4: 118 to 129) and of the CDR (CDR1: 27 to 38, CDR2: 56 to 65; and CDR3: 105 to 117) is provided.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may selected from the group consisting of a Fv, single-chain Fv (scFv; a molecule consisting of $V_L$ and $V_H$ connected with a peptide linker), Fab, F(ab')$_2$, single-domain antibody (sdAb; a fragment composed of a single $V_L$ or $V_H$), and multivalent presentations of any of these. Antibody fragments such as those just described may require linker sequences, disulfide bonds, or other type of covalent bond to link different portions of the fragments; those of skill in the art will be familiar with the requirements of the different types of fragments and various approaches and various approaches for their construction.

In a non-limiting example, the antibody fragment may be an sdAb derived from naturally-occurring sources. Heavy chain antibodies of camelid origin (Hamers-Casterman et al, 1993) lack light chains and thus their antigen binding sites consist of one domain, termed $V_HH$. sdAb have also been observed in shark and are termed $V_{NAR}$ (Nuttall et al, 2003). Other sdAb may be engineered based on human Ig heavy and light chain sequences (Jespers et al, 2004; To et al, 2005). As used herein, the term "sdAb" includes those sdAb directly isolated from $V_H$, $V_HH$, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed by the present invention are homologues, derivatives, or fragments that retain the antigen-binding function and specificity of the sdAb.

Natural camelid sdAb can be advantageous due to their small size, ease of genetic manipulation, high affinity and solubility, overall stability and unique refolding capacity. They possess desirable properties for antibody molecules, such as high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996). Further modifications to increase stability, such as the introduction of non-canonical disulfide bonds (Hussack et al, 2011; Kim et al, 2012), may also be brought to the sdAb.

$V_HH$, which represent a significant amount of antibodies found in camelid, have highly conserved amino acids in specific locations of the framework region 2 (FR2): Phe or Tyr at position 42, Glu at position 49, Arg at position 50, and Gly, Leu, or Trp at position 52, where amino acid positions are numbered according to the IMGT system. These conserved residues not only contribute to reshaping the surface of the antibody (the "interface" region, compared to a conventional antibody) but also play a role in the solubility of the $V_HH$. However, and as known to those of skill in the art, classical $V_H$ fragments have also been isolated from non-immune and immune camelid libraries (Tanha et al, 2002). These conventional sdAb possess consensus amino acids in FR2 as follows: Val at position 42, Gly at position 49, Leu at position 50, and Trp at position 52, where amino acid positions are numbered according to the IMGT system. The isolated or purified antibody or fragment thereof of the present invention comprises the $V_H$ hallmark amino acids in FR2; specifically, Val at position 42, Gly at position 49, Leu at position 50, and Trp at position 52 (according to the IMGT numbering system). Without wishing to be limiting or bound by theory in any manner, the isolated or purified antibody or fragment thereof as described herein lacking the solubilizing residues or typical camelid $V_HH$ hallmark residues may render the antibodies closer to human antibodies, leading to a decreased risk of adverse immunogenicity in humans.

A person of skill in the art would be well-acquainted with the structure of a single-domain antibody. A sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3, and numbered as defined by Lefranc, M. P. et al. (2003; IMGT numbering).

The antibody or fragment thereof of the present invention specifically binds Tau, a member of a family of microtubule-associated proteins and responsible for stabilizing microtubules within the neuronal cytoskeleton. In solution, the protein behaves as a natively unfolded protein. Six tau isoforms exist in human brain tissue, and they are distinguished by their number of binding domains. Three isoforms (3R/2N, 3R/1N, 3R/0N) have three binding domains and the other three (4R/2N, 4R/1N, 4R/0N) have four binding domains. The binding domains are located in the carboxy-terminus of the protein and are positively-charged (allowing it to bind to the negatively-charged microtubule). Tau is a phosphoprotein with numerous potential serine (Ser) and threonine (Thr) phosphorylation sites. Abnormal and excessive phosphorylation has been observed in pathological states, rendering Tau non-functional and disrupting microtubular structure leading to cell death (Ballatore et al, 2007; Avila et al, 2004). More recently abnormal deposition of tau, also termed neurofibrillary tangles, has been associated with the post mortem brains of individuals who sustained multiple repetitive TBI (McKee et al, 2009). The antibody or fragment thereof of the present invention may specifically bind hyper-phosphorylated Tau.

As previously stated, the antibody or fragment thereof may be a sdAb. The sdAb may be selected from the group consisting of sdAb of camelid origin or sdAb derived from a camelid $V_H$ or $V_HH$, and thus may be based on camelid framework regions; alternatively, the CDR described above may be grafted onto a scaffold selected from the group consisting of $V_{NAR}$, $V_HH$, $V_H$ or $V_L$ framework regions. In yet another alternative, the hypervariable loops described above may be grafted onto the framework regions of other types of antibody fragments (selected from the group consisting of Fv, scFv, Fab) of any source (for example, mouse or human) or proteins of similar size and nature onto which CDR can be grafted (for example, see Nicaise et al, 2004).

The present invention further encompasses an antibody fragment that is "humanized" using any suitable method known in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the CDR defined herein may be fused or grafted to a human variable region ($V_H$, or $V_L$), to other human antibody (IgA, IgD, IgE, IgG, and IgM), to antibody fragment framework regions (Fv, scFv, Fab), or to proteins of similar size and nature onto which CDR can be grafted (Nicaise et al, 2004). In such a case, the conformation of said one or more than one hypervariable loop is likely preserved, and the affinity and specificity of the sdAb for its target (i.e., tau) is likely minimally affected. CDR grafting is known in the art and is described in at least the following: U.S. Pat. No. 6,180,370, U.S. Pat. No. 5,693,761, U.S. Pat. No. 6,054,297, U.S. Pat. No. 5,859,205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. No. 5,869,619, U.S. Pat. No. 5,766,886, U.S. Pat. No. 5,821,123, and European Patent No. 519596. Persons of skill in the art would also be amply familiar with methods of preparing such humanized antibody fragments and humanizing amino acid positions.

In a non-limiting example, the antibody or fragment thereof may have a CDR1 sequence of GFTFSNFA (SEQ ID NO:1), a CDR2 sequence of IDNDGGRT (SEQ ID NO:2), and a CDR3 sequence of AAMNLATRKWEL (SEQ ID NO:3). Alternatively, the antibody or fragment thereof may have a CDR1 sequence of GFTGDHYA (SEQ ID NO:4), a CDR2 sequence of IYSYSPNT (SEQ ID NO:5), and a CDR3 sequence of AADLEVAEYYAY (SEQ ID NO:6). The antibody or fragment thereof may specifically bind Tau.

In one specific example, non-limiting example, the isolated or purified antibody or fragment thereof specifically binding Tau may be (SEQ ID NO: 7)
QVKLEESGGGLVQPGGSLRLSCAASGFTFSNFAMTWVRQSPGKGLEWVS

AIDNDGGRTSYSDSVKGRFTISRDNAKNTLYLQMNSLKPEDTAMYYCAA

MNLATRKWELWGQGTQVTVSS, referred to herein as

Tau15;

(SEQ ID NO: 8)
QVQLVESGGGLVQPGGSLKLSCAASGFTGDHYAMSWVRQAPGKGLEWVS

TIYSYSPNTYYVDSVKDRFTISLDNAKNTLYLQMNSLKPEDTAVYYCAA

DLEVAEYYAYWGQGTQVTVSS, referred to herein as

Tau81;

or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations may be made to the framework regions of the sdAb while maintaining the CDR sequences listed above and the overall structure of the CDR of the antibody or fragment; thus the specificity and binding of the antibody are maintained.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 90% identical; in another example, the substantially identical sequences may be selected from the group consisting of at least 90, 91, 92, 93, 94, 95, 96, 97, 98, 99, or 100% identical, or any percentage there between, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, the present invention may be directed to an antibody or fragment thereof comprising a sequence selected from the group consisting of at least 90%, 95%, 98%, or 99% identical to that of the antibodies described herein.

The antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to OmpA), a detection/purification tag (for example, but not limited to c-Myc, $His_5$, or $His_6$), or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

The antibody or fragment thereof of the present invention may also be in a multivalent display format, also referred to herein as multivalent presentation, or multimerized. Multimerization may be achieved by any suitable method known in the art. For example, and without wishing to be limiting in any manner, multimerization may be achieved using self-assembly molecules such as those described in Zhang et al (2004a; 2004b) and WO2003/046560, where pentabodies are produced by expressing a fusion protein comprising the antibody or fragment thereof of the present invention and the pentamerization domain of the β-subunit of an $AB_5$ toxin family (Merritt & Hol, 1995). A multimer may also be formed using the multimerization domains described by Zhu et al. (2010); this form, referred to herein as a "combody", is a fusion of the antibody or fragment of the present invention with a coiled-coil peptide resulting in a multimeric molecule. Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielson et al, 2000), c-jun/Fos interaction (de Kruif & Logtenberg, 1996), "Knob into holes" interaction (Ridgway et al, 1996).

Another method known in the art for multimerization is to dimerize the antibody or fragment thereof using an Fc or a portion of the Fc, for example, but not limited to Fc, $C_{H1}$ domain, $C_{H2}$ domain, $C_{H3}$ domain, the hinge region, or any appropriate combination thereof. The Fc domain or a portion thereof may be of human origin, camelid origin, or other suitable origin. The Fc or fragment thereof may be selected from various classes including, but not limited to, IgG, IgM, or various subclasses including, but not limited to IgG1, IgG2, etc. In this approach, the Fc gene is inserted into a vector along with the sdAb gene to generate a sdAb-Fc fusion protein (Bell et al, 2010; Iqbal et al, 2010); the fusion protein is recombinantly expressed then purified. Such multimerized antibodies are easy to engineer and to produce, can greatly extend the serum half-life of sdAb, and may be excellent tumor imaging reagents (Bell et al., 2010).

The Fc domain in the multimeric complex as just described may be any suitable Fc fragment known in the art. The Fc fragment may be from any suitable source; for example, the Fc may be of an origin selected from the group consisting of mouse and human. In a specific, non-limiting example, the Fc may be selected from the group consisting of the mouse FcT2b fragment and human FcT1 fragment (Bell et al, 2010; Iqbal et al, 2010). In an alternative example, the Fc fragment thereof may be selected from the group consisting of the human hinge region sequence AEPISCDKTHTCPPCP (SEQ ID NO:16) and ETSSPAEPKSCDKTHTCPPCP (SEQ ID NO:17).

Each subunit of the multimers described above may comprise the same or different antibodies or fragments thereof of the present invention, which may have the same or different specificity. Additionally, the multimerization domains may be linked to the antibody or antibody fragment using a linker, as required; such a linker should be of sufficient length and appropriate composition to provide flexible attachment of the two molecules, but should not hamper the antigen-binding properties of the antibody.

Specific, non-limiting examples of dimeric version of the antibody or fragment thereof include those selected from the group consisting of SEQ ID NO:20 (referred to herein as DH-Tau15) and SEQ ID NO:23 (referred to herein as Fc-Tau15).

The antibody or fragment thereof as described herein may transmigrate across the neuronal cell membrane; it is possible that the antibody or fragment thereof as described herein transmigrates across the blood-brain barrier. The brain is separated from the rest of the body by a specialized endothelial tissue known as the blood-brain barrier (BBB). The endothelial cells of the BBB are connected by tight junctions and efficiently prevent many therapeutic compounds from entering the brain. The mechanism by which the sdAb crosses the neuronal cell membrane is currently unknown. Without wishing to be bound by theory, the variability of neuronal membrane pore size (micrometers) and the size of the sdAb-NP complex suggest a type of bulk-phase pinocytotic mechanism.

The present invention also encompasses nucleic acid sequences encoding the molecules as described herein. Given the degeneracy of the genetic code, a number of nucleotide sequences would have the effect of encoding the polypeptide, as would be readily understood by a skilled artisan. The nucleic acid sequence may be codon-optimized for expression in various micro-organisms. The present invention also encompasses vectors comprising the nucleic acids as just described. Furthermore, the invention encompasses cells comprising the nucleic acid and/or vector as described.

The present invention further encompasses the isolated or purified antibody or fragments thereof immobilized onto a surface using various methodologies; for example, and without wishing to be limiting, the antibody or fragment may be linked or coupled to the surface via one selected from the group consisting of His-tag coupling, biotin binding, covalent binding, adsorption, and the like. Immobilization of the antibody or fragment thereof of the present invention may be useful in various applications for capturing, purifying or isolating proteins. The solid surface may be any suitable surface, for example, but not limited to one selected from the group consisting of the well surface of a microtiter plate, channels of surface plasmon resonance (SPR) sensor chips, membranes, beads (such as magnetic-based or sepharose-based beads or other chromatography resin), glass, plastic, stainless steel, a film, or any other useful surface such as nanoparticles, nanowires and cantilever surfaces.

The invention also encompasses the antibody or fragment thereof as described above linked to a cargo molecule. Without wishing to be limiting in any manner, the cargo molecule may be one selected from the group consisting of a detectable agent, a therapeutic agent, a drug, a peptide, an enzyme, a growth factor, a cytokine, a receptor trap, an antibody or fragment thereof (e.g., IgG, scFv, Fab, $V_H H$, $V_H$, $V_L$, etc) a chemical compound, a carbohydrate moiety, DNA-based molecules (anti-sense oligonucleotide, microRNA, siRNA, plasmid), a cytotoxic agent, viral vector (adeno-, lenti-, retro), one or more liposomes or nanocarriers loaded with any of the previously recited types of cargo molecules, one or more nanoparticle, nanowire, nanotube, and quantum dots. The cargo molecule as described above may be a detectable agent; for example, the Tau-specific antibody or fragment thereof may be linked to one selected from the group consisting of a radioisotope, a paramagnetic label, a fluorophore, a fluorescent agent, Near Infra-Red (NIR; for example Cy5.5) fluorochrome or dye, an echogenic microbubble, an affinity label, a detectable protein-based molecule, nucleotide, quantum dot, nanoparticle, nanowire, or nanotube, and any other suitable agent that may be detected by imaging methods. The antibody or fragment thereof may be linked to the cargo molecule using any method known in the art (recombinant technology, chemical conjugation, etc.).

In one non-limiting example, the cargo molecule may be one selected from the group consisting of a detectable label, a radioisotope, a paramagnetic label such as gadolinium or iron oxide, a fluorophore, Near Infra-Red (NIR) fluorochrome or dye, an echogenic microbubble, an affinity label (for example biotin, avidin, etc), enzymes, or any other suitable agent that may be detected by diagnostic imaging methods. In a specific, non-limiting example, the anti-Tau antibody or fragment thereof may be linked to one selected from the group consisting of a near infrared fluorescence (NIRF) imaging dye, for example and not wishing to be limiting Cy5.5, Alexa488, Alexa680, Dylight680, or Dylight800.

The detectable label may be a MRI-visible reagent; the MRI-visible reagent may be a nanoparticle, such as a superparamagnetic nanoparticle. The nanoparticle may be selected from the group consisting of a synthetic, solid, or colloidal particle comprising one selected from the group consisting of macromolecules, semiconductors, metal, oxide fluoride salts, and a combination thereof, in which a desired agent can be adsorbed, entrapped or covalently attached. The nanoparticle may be of a size in the range of 1 to 100 nm; for example, the nanoparticle may of a size selected from the group consisting of be 1, 10, 20, 30, 40, 50, 60, 70, 80, 90, or 100 nm or any size therebetween, or any range of sizes defined by the sized as just defined. In one example, the nanoparticle size may be in the range of about 10 to about 50 nm; in one specific non-limiting example, the nanoparticle size may be 11 or 12 nm.

For example, the MRI-visible reagent may be, but is not limited to one selected from the group consisting of NaDyF4-NaGdF4 core-shell nanoparticles, silica coated ferrous oxide, gold nanoparticles, $\beta$-NaYF$_4$:Yb,Gd,Tm, gadolinium nanoparticle, solid lipid nanoparticles, and any other suitable nanoparticle known in the art. In a specific, non-limiting example, the detectable label is a NaDyF4-NaGdF4 core-shell nanoparticle. The nanoparticle may also be modified to confer a characteristic selected from the group consisting of being inert, targeted to the neuronal cell membrane, non-toxic, able to avoid platelet aggregation, or provide it with prolonged circulation time. Several such mechanisms are known in the art and may include, but not limited to clathrin coating, hollow-nanoporosity, or nanoparticle coating with minimally adhesive PEG.

The isolated antibody or fragment thereof of the present invention may be conjugated to the nanoparticle surface in any appropriate ratio. For example, the number of isolated antibody or fragment thereof on the surface of a nanoparticle may be selected from the group consisting of the range of about 2 to about 25 (ratio of 2:1 to 25:1), or more specifically about 4 to about 22 (ratio of 4:1 to 22:1); for example, the number of isolated antibody or fragment thereof on the surface of a nanoparticle may be selected from the group consisting of 2, 3, 4, 5, 6, 7, 8, 9, 10, 11, 12, 13, 14, 15, 16, 17, 18, 19, 20, 21, 22, 23, 24, or 25, or any range defined by the aforementioned values. In one example, the number of isolated antibody or fragment thereof on the surface of the nanoparticle may be selected from the group consisting of 4, 12, or 22 (ratio of 4:1, 12:1, or 22:1). In a specific, non-limiting example, nanoparticles with 4 isolated antibody or fragment thereof conjugate to their surface may bind to intracellular tau.

The cargo molecule as described herein may be linked, also referred to herein as "conjugated", to the antibody or fragment thereof by any suitable method known in the art. For example, and without wishing to be limiting, the cargo molecule may be linked to the peptide by a covalent bond or ionic interaction. The linkage may be achieved through a chemical cross-linking reaction (such as amine coupling), or through fusion using recombinant DNA methodology combined with any peptide expression system, such as bacteria, yeast or mammalian cell-based systems. When conjugating the cargo molecule to the antibody or fragment thereof, a suitable linker may be used. Methods for linking an antibody or fragment thereof to a cargo molecule such as a therapeutic or detectable agent would be well-known to a person of skill in the art.

The present invention further provides an in vitro method of detecting Tau or hyperphosphorylated Tau, comprising contacting a tissue sample with one or more than one isolated or purified antibody or fragment thereof of the present invention linked to a detectable agent. The Tau-antibody complex can then be detected using detection and/or imaging technologies known in the art. The tissue sample in the method as just described may be any suitable tissue sample, for example but not limited to a brain tissue sample; the tissue sample may be from a human or animal subject. The step of contacting is done under suitable conditions, known to those skilled in the art, for formation of a complex between the antibody or fragment thereof and Tau. The step of detecting may be accomplished by any suitable method known in the art, for example, but not limited to one selected from the group consisting of optical imaging, immunohistochemistry, molecular diagnostic imaging, ELISA, imaging mass spectrometry, and other suitable method. For example, and without wishing to be limiting in any manner, the isolated or purified antibody or fragment thereof linked to a detectable agent may be used in immunoassays (IA) including, but not limited to one selected from the group consisting of enzyme IA (EIA), ELISA, "rapid antigen capture", "rapid chromatographic IA", and "rapid EIA". (For example, see Planche et al, 2008; Sloan et al, 2008; Rüssmann et al, 2007; Musher et al, 2007; Turgeon et al, 2003; Fenner et al, 2008).

As previously discussed, pathological states (for example but not limited to Alzheimer's disease and traumatic brain injury) have been linked with the abnormal localization of tau, particularly hyper-phosphorylated tau. This results in an accumulation of hyper-phosphorylated tau as neurofibrillary tangles, which can lead to impairment of brain function. Thus, the present invention also provides an in vivo method of visualizing Tau localization in a subject; the subject may have or be suspected of having a pathological condition such as, but not limited to Alzheimer's disease or a traumatic brain injury. The method comprises administering one or more than one isolated or purified antibody or fragment thereof as described herein linked to a detectable agent to the subject, then detecting the labelled antibody or fragment thereof bound to tau. The step of detecting may comprise any suitable method known in the art, for example, but not limited to one selected from the group consisting of PET, SPECT, MRI, fluorescence imaging, and any other suitable method. As would be known in the art, the method of detecting will be related to the type of detectable label used. The method as just described may be useful in visualizing the brain in various situations, for example selected from the group consisting of a subject suspected of having a pathological condition; to evaluate whether a subject has a pathological condition; or to monitor the progression of or recovery from a pathological condition.

The in vivo detection step in the methods described above may be whole body imaging for diagnostic purposes or local imaging at specific sites, such as but not limited to brain vessels or brain tumor vessels, in a quantitative manner to assess the progression of disease or host response to a treatment regimen. The detection step in the methods as described above may be selected from the group consisting of immunohistochemistry, and a non-invasive (molecular) diagnostic imaging technology including, but not limited to one selected from the group consisting of:

Optical imaging;

Positron emission tomography (PET), wherein the detectable agent is an isotopes such as $^{11}C$, $^{13}N$, $^{15}O$, $^{18}F$, $^{64}Cu$, $^{62}Cu$, $1^{24}I$, $^{76}Br$, $^{82}Rb$ and $^{68}Ga$, with $^{18}F$ being the most clinically utilized;

Single photon emission computed tomography (SPECT), wherein the detectable agent is a radiotracer such as $^{99m}Tc$, $^{111}In$, $^{123}I$, $^{201}Tl$, $^{133}Xe$, depending on the specific application;

Magnetic resonance imaging (MRI), wherein the detectable agent may be, for example and not limited to gadolinium, iron oxide nanoparticles and carbon-coated iron-cobalt nanoparticles thereby increasing the sensitivity of MRI for the detection of plaques; and Contrast-Enhanced Ultrasonography (CEUS) or ultrasound, wherein the detectable agent is at least one acoustically active and gas-filled microbubble. Ultrasound is a widespread technology for the screening and early detection of human diseases. It is less expensive than MRI or scintigraphy and safer than molecular imaging modalities such as radionuclide imaging because it does not involve radiation.

In a non-limiting example, the method comprises administering one or more than one isolated or purified antibody or fragment thereof as described herein linked to a MRI-visible nanoparticle to the subject, then detecting the labelled antibody or fragment thereof bound to tau using combined T2 and T1 weighted MRI. In a specific example, which is not intended to be limiting in any manner, the MRI-visible nanoparticle is NaDyF4-NaGdF$_4$ core-shell nanoparticles.

The present invention further provides a method of transporting a molecule of interest across the neuronal cell membrane. The method comprises administering the molecule linked to an antibody or fragment thereof as described herein to a subject; the antibody or fragment thereof transmigrates the neuronal cell membrane. The molecule may be any desired molecule, including the cargo molecules as previously described; the molecule may be "linked" to the antibody or fragment thereof using any suitable method, including, but not limited to conjugation or expression in a fusion protein. The administration may be by any suitable method, for example parenteral administration, including but not limited one selected from the group consisting of to intravenous (iv), subcutaneous (sc), and intramuscular (im) administration. In this method, the antibody or fragment thereof of the present invention 'ferries' the molecule of interest across the neuronal cell membrane to its brain target.

The present invention also encompasses a composition comprising one or more than one isolated or purified antibody or fragment thereof as described herein; the antibody or fragment thereof may optionally be linked to a cargo molecule, such as a detectable label, as described herein. The composition may comprise a single antibody or fragment (optionally linked to a cargo molecule) as described above, or may be a mixture of antibodies or fragments. Furthermore, in a composition comprising a mixture of antibodies or fragments of the present invention (optionally linked to a cargo molecule), the antibodies may have the same specificity, or may differ in their specificities; for example, and without wishing to be limiting in any manner, the composition may comprise antibodies or fragments thereof specific to tau.

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in a form selected from the group consisting of suspension form, powder form (for example, but limited to lyophilised or encapsulated), capsule or tablet form. For example, and without wishing to be limiting, when the composition may be provided in suspension form, the carrier may comprise one selected from the group consisting of water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody or fragment thereof to the gastrointestinal tract of the subject. Thus, the composition may comprise encapsulation, time-release, or other suitable technologies for delivery of the antibody or fragment thereof. It would be within the competency of a person of skill in the art to prepare suitable compositions comprising the present compounds.

The present inventors have isolated two monomeric anti-tau sdAb from llama immunized with a recombinant tau protein. Tau15 and Tau81 showed micromolar affinity binding to tau, with Ko ranging from 0.7 µM to 0.8 µM, and similar binding affinities for hyper-phosphorylated tau. While Tau15 and Tau81 were isolated from llama, the sdAb bear the sequence hallmarks of $V_H$, rather than the $V_H H$ typically isolated from camelid libraries. As the isolated sdAb lack the typical camelid solubilizing residues at known positions, they may exhibit decreased immunogenicity in humans. Reversion of these residues to the sdAb consensus abrogated binding to tau in all of the sdAb, but did not impair their expression as folded monomers (data not shown), suggesting that these residues play a critical role in binding despite their location in framework regions.

The sdAb were amine-coupled to $NaDyFy$-$NaGdF_4$ core-shell nanoparticles (NP) tagged to a fluorescent marker (Alexa488), which allowed the complex to be evaluated in vitro via fluorescent microscopy. Preliminary in vitro testing using both fixed and live hippocampal neuronal cultures successfully demonstrated intracellular binding of the sdAb-NP-Alexa488 complex (4:1 sdAb:NP ratio) to tau protein. These data demonstrate the ability of the complex to cross the neuronal membrane and bind to intracellular tau. Tau15 also showed binding to intracellular hyper-phosphorylated tau.

The ability of the sdAb-nanoparticle complex, which has a hydrodynamic diameter of ~40 nm, to cross the neuronal cell membrane and bind to intracellular tau is surprising. The highly robust antigen recognition and specificity of the sdAb nanoparticle complex, along with its electrical charge and possibly altered morphology as a complex, may influence the ability of the sdAb-NaDyF4-NaGdF4 nanoparticle to cross cellular membranes.

The present invention thus provides a novel tool for intra-neuronal, non-invasive imaging of tau and hyper-phosphorylated tau. The ability of the sdAb-NaDyF4-NaGdF4 complex to cross the cell membrane and bind to intracellular tau is significant, allowing for its use in visualization of pathological conditions such as traumatic brain injury and neurodegenerative disorders (for example Alzheimer's disease). Thus, the complex may assist in early diagnosis and monitoring disease progression in these types of conditions.

The present invention will be further illustrated in the following examples. However, it is to be understood that these examples are for illustrative purposes only and should not be used to limit the scope of the present invention in any manner.

Example 1: Llama Immunization and Serum Response

To isolate $V_H H$ that targets tau, a llama was immunized with a recombinant human tau protein, isoform 2N4R. This recombinant Tau-441 protein (molecular weight 45.9 kDa) was purchased from Sigma Aldrich.

One male llama (*Lama glama*) was immunized by subcutaneous injection of recombinant Tau-441 protein (Sigma-Aldrich, USA). On day 1, the llama was injected with 200 µg of Tau-441, in a total volume of 0.5 mL mixed with an equal volume of complete Freund's adjuvant (Sigma, St. Louis, Mo.). Four further injections of 100 µg of Tau-441 plus Freund's Incomplete Adjuvant (Sigma) were performed on days 21, 28, 35 and 42, again along with three other human proteins. Pre-immune blood was drawn before the first injection on day 1 and served as a negative control. Blood was collected on day 47. The blood from day 47 was processed immediately to isolate peripheral blood lymphocytes (PBL). The blood was diluted 1:1 with phosphate buffered saline (PBS) and PBL were purified from the blood using the Lymphoprep Tube (Axis-Shield, Norway). The cells were counted and stored as aliquots of about $1 \times 10^7$ cells at −80° C. for future use.

The polyclonal immune responses of pre-immune and post-immune total serum as well as conventional and heavy chain antibody fractions obtained by protein A and G chromatography (as described in Baral et al, 2013) were analyzed by ELISA. Briefly, 96-well Maxisorp™ plates (Nalgene Nunc International, USA) were coated overnight at 4° C. with 10 µg/mL of Tau-441 antigen in PBS. Wells were rinsed and blocked with 200 µl of 1% casein. Different dilutions of pre-immune, immune, and purified IgG fractions (G1, G2, A1 and A2) were added and incubated at room temperature for 1.5 h. Wells were washed with PBS with 0.05% Tween-20, and incubated with goat anti-llama-HRP (1:10,000 in PBS) (Cedarlane Laboratories Ltd., Canada). Binding was detected by adding 100 µl Tetramethylbenzidine (TMB) peroxidase substrate per well (Kirkegaard and Perry Laboratories, USA). Reactions were stopped by adding 100 µl 1M phosphoric acid and A450 was measured using a Bio-Rad ELISA plate reader.

ELISA analysis of the binding of the total and fractionated serum showed strong immune responses in the total and conventional antibody fractions (G2) when compared to the pre-immune serum. However, all three heavy chain antibody fractions (G1, A1 and A2) showed weak immune responses to tau (FIG. 1). To further assess the immunogenicity potential of tau, the same llama was boosted twice more with tau antigen only and the total as well as the fractionated sera were analyzed by ELISA (data not shown). The immune response curves from the final cocktail immunization showed no significant difference from those obtained after two additional boosts with tau.

Example 2: Library Construction and Selection of Tau-Binding sdAb

A immune $V_H H$ library was constructed based on RNA isolated from the PBL collected in Example 1.

A phage display library was constructed as previously described (Baral et al, 2013). In brief, total RNA was isolated from approximately $1\times10^7$ lymphocytes collected on day 47 using a QIAamp RNA blood mini kit (Qiagen, Canada). First-strand cDNA was synthesized with an oligo (dT) primer using 5 µg total RNA as template according to the manufacturer's recommendations (GE Healthcare). The cDNA was amplified by an equimolar mix of three variable region-specific sense primers:

```
                                          (SEQ ID NO: 9)
MJ1:   5'-GCCCAGCCGGCCATGGCCSMKGTGCAGCTGGTGGAKTCTGG
       GGGA-3'

(SEQ ID NO: 10)
MJ2:   5'-GCCCAGCCGGCCATGGCCCAGGTAAAGCTGGAGGAGTCTGG
       GGGA-3'

(SEQ ID NO: 11)
MJ3:   5'-GCCCAGCCGGCCATGGCCCAGGCTCAGGTACAGCTGGTGGA
       GTCT-3',
``` and two antisense $CH_2$-specific primers:

```
                                          (SEQ ID NO: 12)
CH2:       5'-CGCCATCAAGGTACCAGTTGA-3'

(SEQ ID NO: 13)
CH2b3:     5'-GGGGTACCTGTCATCCACGGACCAGCTGA-3'.
```

The PCR reaction mixture and PCR protocol utilized were as described in Baral et al (2013). Briefly, the PCR reaction mixture was set up in a total volume of 50 µl with the following components: 1-3 µl cDNA, 5 pmol of MJ1-3 primer mixture, 5 pmol of $CH_2$ or $CH_2b_3$ primers, 5 µl of 10× reaction buffer, 1 µl of 10 mM dNTP, 2.5 unit of Taq DNA polymerase (Hoffmann-La Roche). The PCR protocol consisted of an (i) initial step at 94° C. for 3 min, (ii) followed by 30 cycles of 94° C. for 1 min, 55° C. for 30 s, 72° C. for 30 s and (iii) a final extension step at 72° C. for 7 min.

The heavy chain fragments (550-650 bp in length) were gel-purified using a QIAquick gel extraction kit (Qiagen) as previously described (Baral et al, 2013). The variable regions of the heavy chain antibodies (IgG2 and IgG3) were re-amplified in a second PCR reaction using oligonucleotides

```
                                          (SEQ ID NO: 14)
MJ7:   5'-CATGTGTAGACTCGCGGCCCAGCCGGCCATGGCC-3'
and
                                          (SEQ ID NO: 15)
MJ8:   5'-CATGTGTAGATTCCTGGCCGGCCTGGCCTGAGGAGACGGTG
       ACCTGG-3'
``` and methods as described above.

The amplified PCR products were purified with a QIAquick PCR purification kit (Qiagen), digested with SfiI (New England Biolabs, Canada), and re-purified using the same kit.

80 µg of pMED1 phagemid vector (Arbabi-Ghahroudi et al, 2009b) were digested with SfiI overnight at 50° C. To minimize self-ligation, 20 units of XhoI and PstI restriction enzymes were added to cut the excised fragment and the digestion reaction was incubated for an additional 2 h at 37° C. Twelve micrograms of digested VHH DNA were ligated with 40 µg (3:1 molar ratio) SfiI-digested pMED1 phagemid vector using LigaFast Rapid DNA ligation system (Promega, USA) using methods previously described (Baral et al, 2013). The ligated plasmids were purified using the QIAquick PCR Purification Kit (Qiagen), eluted in a final volume of 100 µl, and transformed into electrocompetent TG1 *E. coli* (Stratagene) using 5 µl of ligated DNA aliquot per 100 µl transformation reaction, as previously described (Arbabi-Ghahroudi et al, 2009b). The resulting library was of approximately $1\times10^7$ transformants. The $V_HH$ fragments from 30 colonies were PCR-amplified and sequenced to analyze the complexity of the library. The library was expanded by culturing for 3-4 h in 2×YT/ampicillin (100 µg/mL)/glucose (2% w/v) medium at 37° C. The bacterial cells were pelleted, re-suspended in the same medium with 20% glycerol and stored at −80° C.

Panning was performed for a total of four rounds against the tau antigen. Briefly, 1 mL of the library stock ($5\times10^{10}$ bacterial cells) was grown for 1-2 h at 37° C., with shaking at 250 rpm in 2× YT/Amp-Glucose (2% w/v) medium ($A_{600}$=0.4-0.5). The *E. coli* were subsequently infected with 20× excess M13KO7 helper phage (New England Biolabs) for 1 h at 37° C. The culture was then centrifuged at 4° C. and infected bacterial pellets were re-suspended in 200 ml of 2× YT/Amp with 50 µg/ml kanamycin and incubated at 37° C. and 250 rpm. The phage particles in the culture supernatant were incubated with ⅕ volume of 20% PEG 8000/ 2.5M NaCl on ice for 1 h and centrifuged at 10,000 rpm for 15 min. The phage pellets were re-suspended in 2.0 ml of sterile PBS, titrated and used as input phage for panning.

For panning round 1, 96-well Maxisorp™ plates were coated with 40 µg Tau-441 antigen per well overnight at 4° C.; the wells were rinsed with PBS and blocked with PBS/1% (w/v) casein for 2 h at 37° C. Approximately $10^{12}$ phages were added to the blocked wells and incubated for 2 h at 37° C. After washing 5× with PBS/0.1% Tween-20 and 5× with PBS, the bound phages were eluted with 0.1 M triethylamine neutralized with 1M Tris-HCl, pH 7.4, then used to infect exponentially growing TG1 *E. coli*. After 30-60 min incubation at 37° C., the cells were superinfected with M13KO7, incubated for an additional 30 min and grown overnight in 2× YT containing ampicillin (100 µg/mL) and kanamycin (50 µg/mL) at 37° C. The purified phage from the overnight culture was used as the input for the next round of panning. Panning was continued for three more rounds. The same protocol as described above was used, except that the amount of recombinant antigen used to coat the plates was reduced to 30, 20, 20 µg/well and the washing cycle was increased to 7, 10, and 12× with PBS-T and PBS for the second, third and fourth rounds of panning, respectively.

After four rounds of panning, individual TG1 colonies were subjected to phage ELISA screening, essentially as described elsewhere (Baral et al, 2013). All positive clones were sequenced. Unique clones that gave high phage ELISA signals were selected for large-scale expression and purification using known methods (see Example 3). Two clones (Tau15 and Tau81) were identified for further study; their sequences are shown below.

```
                                          (Tau15; SEQ ID NO: 7)
QVKLEESGGGLVQPGGSLRLSCAASGFTFSNFAMTWVRQSPGKGLEWVS

AIDNDGGRTSYSDSVKGRFTISRDNAKNTLYLQMNSLKPEDTAMYYCAA

MNLATRKWELWGQGTQVTVSS (Tau81; SEQ ID NO: 8)
QVQLVESGGGLVQPGGSLKLSCAASGFTGDHYAMSWVRQAPGKGLEWVS

TIYSYSPNTYYVDSVKDRFTISLDNAKNTLYLQMNSLKPEDTAVYYCAA

DLEVAEYYAYWGQGTQVTVSS
```

Of the clones subjected to phage ELISA, all but one showed strong binding to tau; no cross-reactivity or non-specific binding was observed for the blocking buffer or other components of the ELISA. Sequencing data for the clones showed that the sdAb had a signature of camelid VH.

Example 3: Expression and Purification of Selected $V_HH$ Constructs

Anti-tau $V_HH$ identified in Example 2 were sub-cloned into expression plasmids for protein expression and purification.

The $V_HH$ genes for Tau15 and Tau81 were sub-cloned in pSJF2H expression vector between BbsI and BamHI restriction enzyme sites by GenScript (USA). The final construct included an OmpA leader sequence for secretion of sdAb proteins to the periplasmic space of E. coli, and a cmyc and $His_6$ tags for ease of purification, at the C-terminus of the sdAb.

Large-scale protein expression and purification was performed essentially as previously described (Baral et al, 2013). Briefly, individual colonies were grown (25 mL LB-Amp overnight at 37° C. The pre-culture was used to seed 1 liter 2x YT-Amp culture and grown at 37° C. with vigorous shaking. At OD600=0.7, the cultures were induced by the addition of IPTG to a final concentration of 1 mM. The culture was grown overnight at 28° C. The bacteria were pelleted by centrifuging at 6000 rpm for 12 min, then submitted to cold osmotic shock to extract sdAb from the periplasmic space. The pellet was re-suspended in 30 ml of cold TES buffer (0.2M Tris-Cl pH 8.0, 20% sucrose, 0.5 mM EDTA). The suspension was incubated on ice and vortexed every 10 min for 1 h. Then 40 ml of cold TES (⅛ volume of total volume) was added and immediately vortexed for 1 minute and for 15 seconds every 10 min thereafter for 1 h to extract the protein from the periplasm.

The periplasmic extracts containing sdAb were dialyzed overnight against buffer (20 mM phosphate buffer (pH 7.4), 0.5 M NaCl, 10 mM imidazole) at 4° C. then filtered through a 0.45 μm membrane (EMD Millipore, Canada). Filtered supernatant was loaded onto nickel-charged 5 mL HisTrap™ FF column (GE Healthcare, Canada) and fractionation was performed on an ÄKTA FPLC purification system (GE Healthcare). The sdAb were eluted using gradient elution (buffer containing 500 mM imidazole); the fractions were pooled and dialyzed against PBS. sdAb concentrations were determined by absorbance measurements at 280 nm using theoretical MW and extinction coefficients calculated with the ExPASy ProtParam Tool (expasy.org/tools/protparam.html).

Figure 2A:
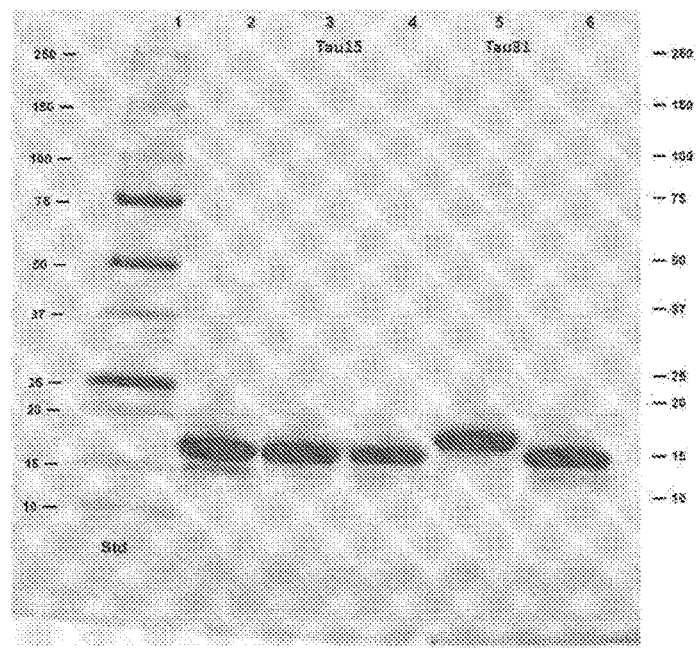
FIG. 2A shows Commassie-stained SDS-PAGE of the expressed and purified sdAb in pSJF2 expression vector. Lane 1, molecular weight markers; lane 2, a non-specific $V_H$; lane 3, 3Tau15 (Tau15); lane 4, a non-specific $V_H$; lane 5, 7Tau81 (Tau81); lane 6, a non-specific $V_H$ (~5 μg/lane). The sdAbs ran at their expected molecular weights.
Figure 2B:
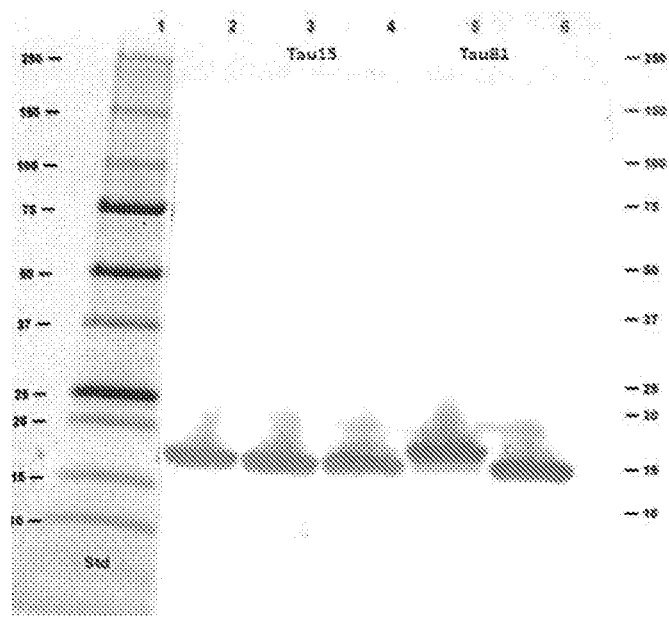
FIG. 2B shows Western blotting detection of the same sdAb proteins using mouse anti-6His-AP conjugate.

Purity of the sdAb was assessed by SDS-PAGE and Western blot; results are shown in FIG. 2.

Figure 3:
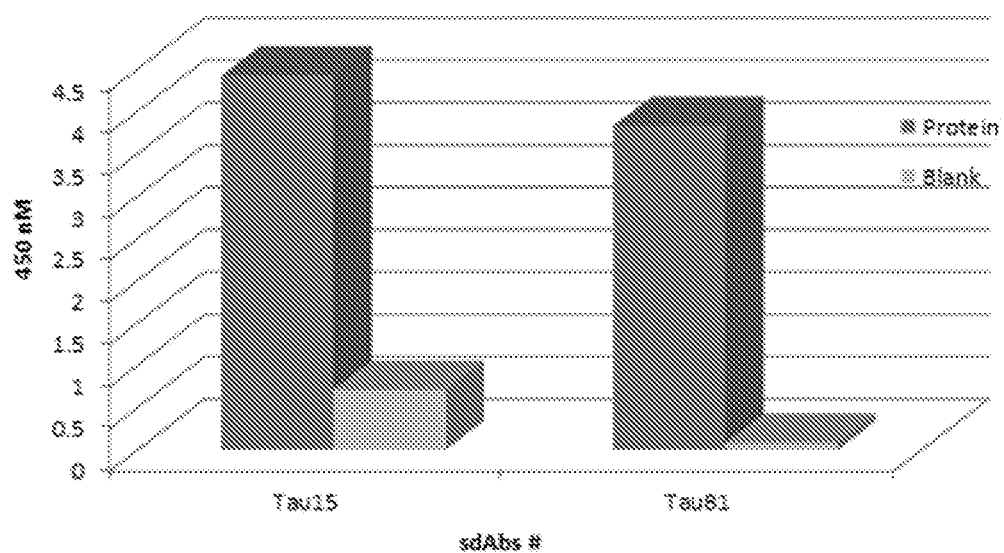
FIG. 3 is a bar graph showing results of protein ELISA. Tau15 and Tau81 showed strong signals.

Protein ELISA was performed for various clones. Briefly, ELISA wells were coated in duplicate with Tau-441 (at 5 μg/mL) overnight at 4° C. and blocked with blocking buffer (1% (w/v) casein-PBS; pH 7.4) for 2 h. The sdAb extracted from the bacterial periplasm (Tau81 and Tau15,) were added (100 ul) to the blocked wells and incubated for additional 2 h at room temperature. Bound sdAb were detected using a rabbit anti-6His-HRP conjugate (at 1:5000 dilution) and one hour incubation time at room temperature. The signal was read at 450 nm using an ELISA plate reader. The results of protein ELISA are shown in FIG. 3, where Tau15 and Tau81 clearly show strong binding signals.

Example 4: Biophysical Characterization of Anti-Tau sdAb

The Tau15 and Tau81 constructs expressed and purified in Example 3 were characterized using size exclusion chromatography, surface plasmon resonance analysis, and melting temperature analysis.

Figure 4A:
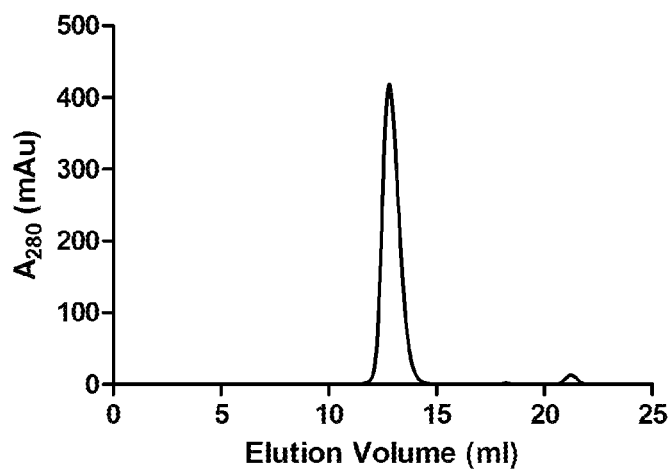
FIG. 4 shows size-exclusion chromatography profiles of purified sdAb Tau15 (FIG. 4A) and Tau81 (FIG. 4B) injected at ~20 μM concentrations. sdAb Tau15 and Tau81 are mainly non-aggregating monomers, though minimal aggregation (less than 10%) is observed for Tau81. A typical gel filtration/size exclusion chromatogram of a uniquely monomeric sdAb is shown in FIG. 4C.
Figure 4B:
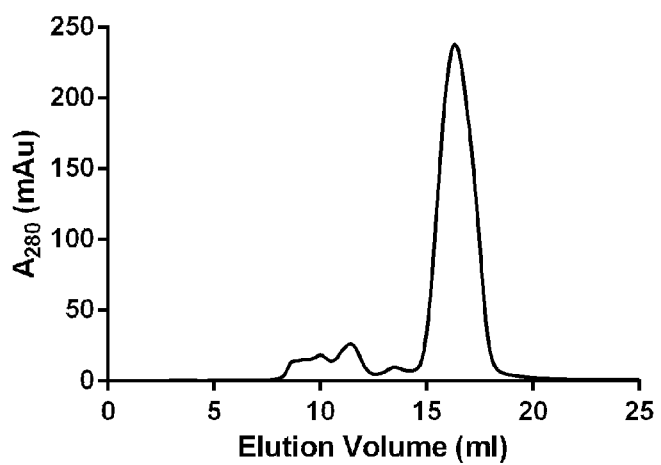
Figure 4C:
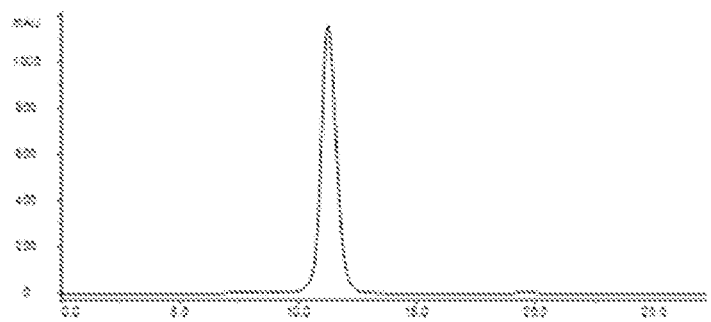

Size Exclusion Chromatography:

Size exclusion chromatography employing Superdex™ 75 10/300 GL (GE Healthcare) was used to eliminate any possible aggregates prior to Surface Plasmon Resonance (SPR) analysis. The running buffer used was HBS-EP+ buffer (10 mM HEPES, pH7.4 containing 150 mM NaCl, 3 mM EDTA and 0.005% P20 surfactant), at a flow rate of 0.5 mL/min. Concentrations of fractions used for SPR analysis were determined to be 1.14 to 2.0 mg/mL by measuring absorbance at 280 nm wavelength. The SEC analysis suggested that the antibodies were monomeric, based on the elution volume compared to standards (FIG. 4).

Surface Plasmon Resonance (SPR):

All binding assays for Tau15 and Tau81 were carried out at 25° C. on a Biacore™ T200 instrument (GE Healthcare). For binding analysis, approximately 1065 resonance units (RUs) of Tau-441 (Sigma Aldrich) or hyperphosphorylated tau (tau-p; University of Victoria) diluted in 10 mM acetate buffer pH 5.0 were immobilized on a CM5 Series S sensor chip (GE Healthcare) using an amine coupling kit (GE Healthcare). Monomeric sdAb (Example 4) were injected over immobilized Tau-441 at a concentration of 500 nM for the test run and concentrations ranging from 50-6000 nM (Tau-441) or 20-6000 nM (for tau-p) for steady state analysis. The running buffer for all SPR experiments was HBS-EP+ (10 mM HEPES, 150 mM NaCl, 3 mM EDTA, pH 7.4, 0.05% surfactant P20; GE Healthcare). The sdAb were injected at 20 μL/min for 3 min with a dissociation time of 7 min for the test run, and at 20 μL/min for 2 min with a dissociation time of 6 min for the steady state analysis. Data was analyzed using the Biacore T200 evaluations software Version 2.0.

Figure 5:
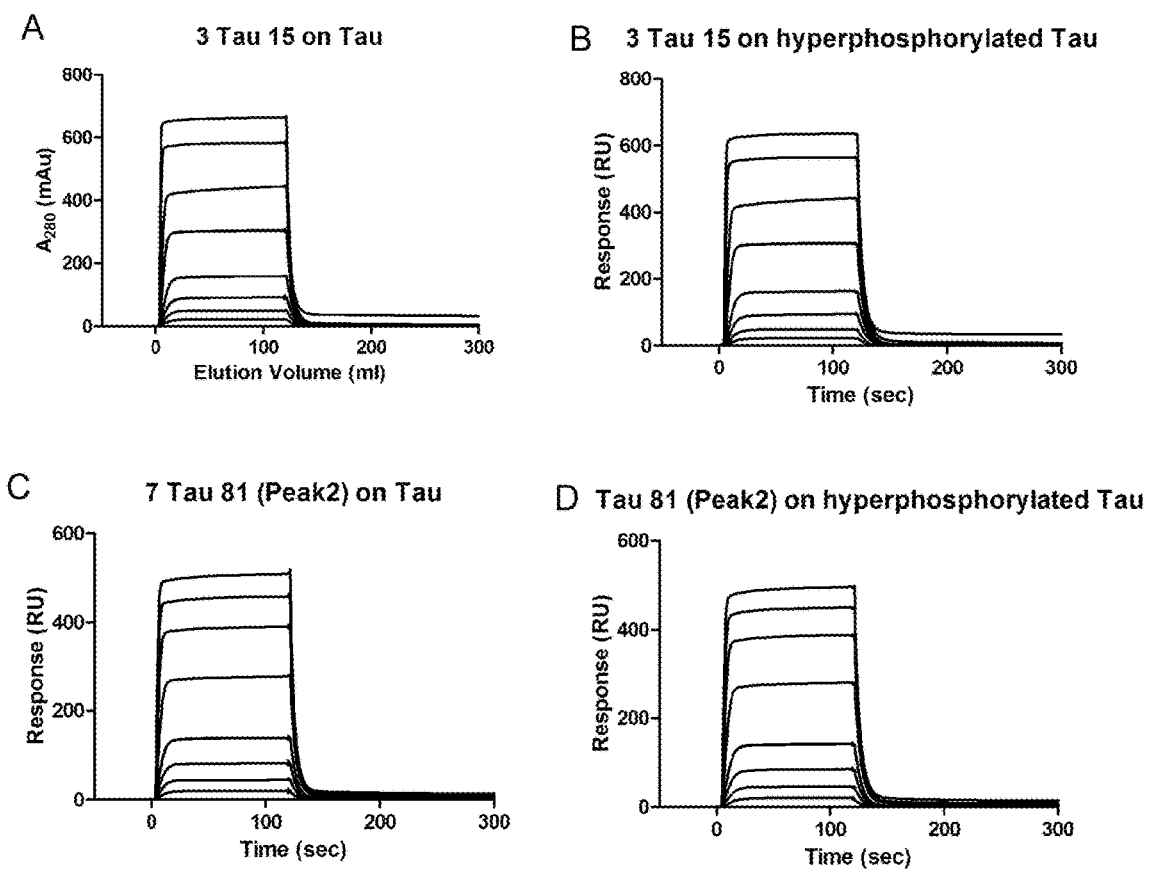
FIG. 5 shows results of SPR analysis of the binding of the monomeric sdAb to tau and tau-p. Sensorgram overlays of monomeric sdAb injected over immobilized tau at concentrations ranging from 50-6000 nM (for tau) and from 20-6000 nM (for tau-p) and steady state analysis of binding to 650-750 RUs of tau and tau-p antigens captured on an SA sensorchip. Under the conditions tested, Tau15 showed an affinity of 0.7 μM (FIG. 5A) to tau and 0.6 μM to tau-p (FIG. 5B). Tau 81 showed an affinity of 0.8 μM to tau (FIG. 5C) and 0.75 μM to tau-p (FIG. 5D).
Figure 6A:
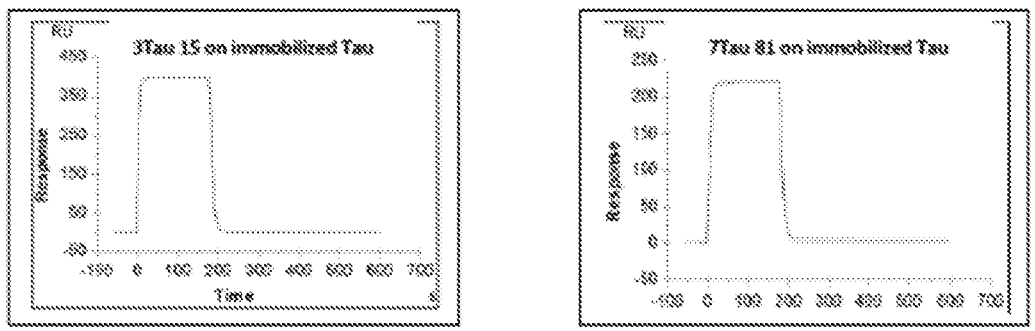
FIG. 6 shows results of SPR analysis of monomeric sdAb over time. Stability measurements of Tau15 and Tau81 were taken after stored at 4° C. for 30 (FIG. 6A), 34 (FIG. 6B), 42 (FIG. 6C), and 55 days (FIG. 6D) following purification. No change in binding behaviour was observed for Tau15 and Tau81.
Figure 6B:
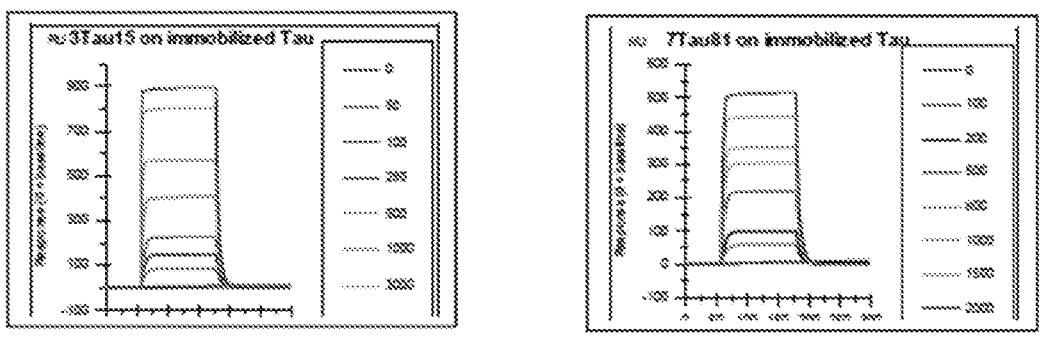
Figure 6C:
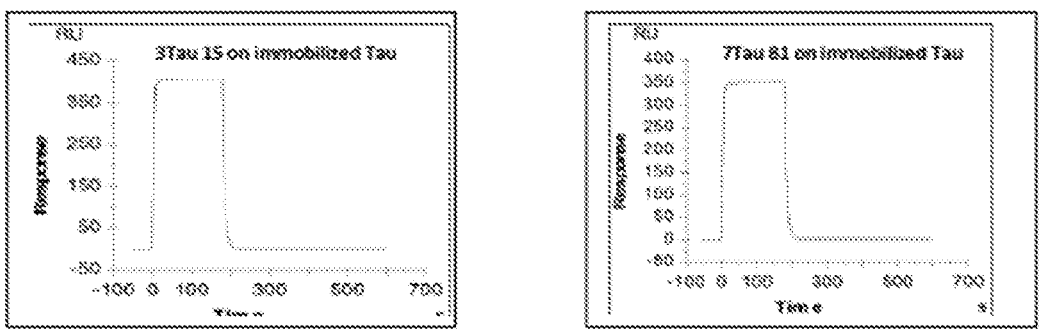
Figure 6D:
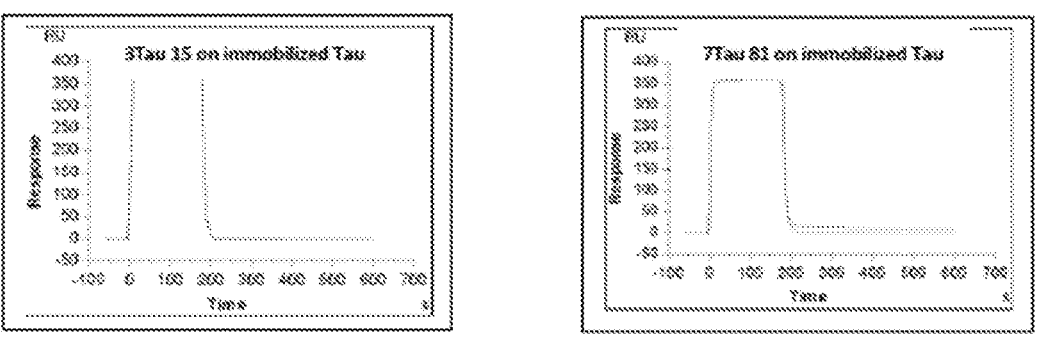

Results of SPR analysis are shown in FIG. 5. sdAb Tau15 and Tau81 showed binding to tau with a fast on and fast off rate. The results show a monovalent interaction of Tau 15 and Tau81 with tau, with both sdAb fitting the Langmuir-equation based 1:1 binding model. The $K_D$ value for the interaction between Tau15 and Tau81 sdAb and immobilized tau were derived by fitting the data to a steady state model and are reported in Table 1. As shown, the two sdAb had micromolar affinity binding to tau, with Ko ranging from 0.7 μM to 0.8 μM. Under the same conditions, Tau15 showed an affinity of 0.6 μM to tau-p, while Tau81 showed an affinity of 0.75 μM to tau-p. Size exclusion chromatograms (FIG. 4) confirmed that Tau15 and Tau81 were monomeric.

TABLE 1

Affinity of anti-tau sdAb for tau and hyperphosphorylated tau.

| sdAb | Protein | $K_D$ (M) | $R_{max}$ (RU) |
|------|---------|-----------|----------------|
| Tau15 | tau | $6.99 \times 10^{-7}$ | 733.4 |
| Tau15 | tau-p | $6.22 \times 10^{-7}$ | 699.0 |
| Tau81 | tau | $8.20 \times 10^{-7}$ | 710.4 |
| Tau81 | tau-p | $7.45 \times 10^{-7}$ | 674.9 |

Stability Studies:

To examine the stability and aggregation tendency of sdAb Tau 15 and Ta81, samples of each were maintained at a concentration of 500 nM at 4° C. until 30, 34, 42, 55 days following initial IMAC purification. The sdAb samples were submitted to SEC and SPR analysis, both as described above. No evidence of aggregation or loss of binding activity was observed upon long term storage at 4° C. (FIG. 6; Table 2).

TABLE 1

Affinity of anti-tau sdAb for tau following incubation at 4° C.

| sdAb | Protein | Days after IMAC purification | $K_D$ (M) | $R_{max}$ (RU) |
| --- | --- | --- | --- | --- |
| Tau15 | tau | 30 | $6.05 \times 10^{-7}$ | 860.20 |
| Tau15 | tau | 34 | $8.20 \times 10^{-7}$ | 958.80 |
| Tau15 | tau | 42 | $5.34 \times 10^{-7}$ | 824.50 |
| Tau15 | tau | 55 | $5.90 \times 10^{-7}$ | 780.10 |
| Tau81 | tau | 30 | $1.05 \times 10^{-7}$ | 673.00 |
| Tau81 | tau | 34 | $1.75 \times 10^{-7}$ | 985.50 |
| Tau81 | tau | 42 | $6.6 \times 10^{-7}$ | 801.90 |
| Tau81 | tau | 55 | $5.07 \times 10^{-7}$ | 696.60 |

Melting Temperature:

The thermal stability of the Tau15 and Tau81 was evaluated using melting temperature ($T_m$) measurement by CD spectroscopy. A Jasco J-815 spectropolarimeter equipped with a Peltier thermoelectric type temperature control system (Jasco, USA) was used to carry out experiments. Filter sterilized buffer (0.1M sodium phosphate buffer, pH 7.3, stored at room temperature) was used. Briefly, 0.2 mL of 50 µg/mL Tau15 and Tau81 was separately tested in a 1 mm quartz (OS) cuvette, pre-cleaned with Hellmanex II quartz cleaning solution 2% (Hellmanex). A test scan on sdAb Tau15 was performed to determine the optimum wavelength to use in the assay. Three accumulations were collected between 190 nm-205 nm with a 1 mm bandwidth, 20 nm/min scan speed and 1 nm data pitch. Based on the data generated from this test scan, wavelengths 200 nm and 205 nm were selected due to the large difference in ellipticity between folded and unfolded states at these wavelengths. Thermal unfolding was measured at 200 and 205 nm with CD measurements taken from 25° C. to 96° C. Raw ellipticity data (mdeg) was exported and converted to molar ellipticity, [θ]. $T_m$ (thermal unfolding midpoint temperature) was obtained by using the sigmoidal Boltzmann function in GraphPad Prism (GraphPad Software, USA) to fit the data.

Figure 7:
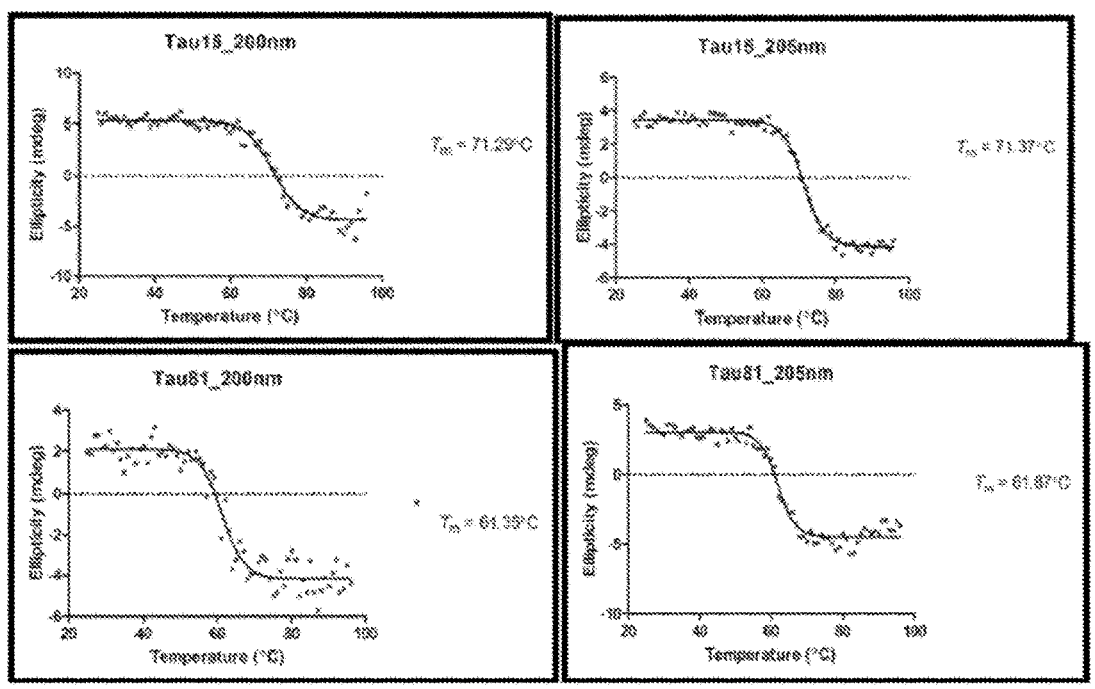
FIG. 7 shows the thermal unfolding curves of Tau15 an Tau81 at neutral pH (7.3). sdAb unfolding was measured using protein concentrations of 50 μg/mL with a circular dichroism spectrometer.

Results are shown in FIG. 7. The thermal unfolding mid-point temperature ($T_m$) of Tau15 was determined to be 71.3° C. at 200 nm and 71.4° C. at 205 nm, while that of Tau81 was determined to be 61.4° C. at 200 nm and 61.9° C. at 205 nm. These data shows that the two isolated sdAb have $T_m$ in the range of those reported for other naturally-occurring camelid sdAb/$V_H$H.

Example 5: Production and Characterization of Nanoparticles

Surface-modified lanthanide (or rare earth) based nanoparticles were produced and bioconjugated to the sdAb of Example 3. Colloidal NaDyF4-NaGdF4 core-shell nanoparticles were selected for the independent optimization of T1 and T2 sequences for enhanced magnetic resonance (MR) visibility, since T1 is most affected by surface $Gd^{3+}$ ions and T2 relaxation time by the "bulk" magnetization of the $Dy^{3+}$ core. Additionally, the proposed nanoparticles can be made with minimal polydispersities in the size of the core and a controlled shell thickness of less than 1 nm. Finally, the synthesis of these nanoparticles is highly reproducible—it can be carried out at >100 mg with easy surface modification for water-dispersibility and subsequent chemical modification. Nanoparticles were prepared at the University of Victoria.

Synthesis of Cubic (α) Phase NaGdF4 Nanoparticles:

Gadolinium oxide (1.0 mmol) was added to 10 mL of 50% trifluoroacetic acid in a three-necked 100 mL round bottom flask and was refluxed at 85° C. for 5 h (Johnson et al, 2012). Excess water was evaporated at 65° C. overnight to yield gadolinium trifluoroacetate. 5 mL oleic acid, 5 mL oleylamine and 10 mL 1-octadecene were added to it and heated at 120° C. for 45 min under vacuum to remove residual water and oxygen. Subsequently, the solution was heated to 285° C. under argon and stirred vigorously for 45 min. The solution was cooled to room temperature. The nanoparticles were precipitated, washed in ethanol, centrifuged at 7000 g (Beckman Coulter Spinchron 15-rotor F0830) for 5 min, and finally dispersed in hexane.

Synthesis of Hexagonal (β) Phase NaDyF4/NaGdF4 Core/Shell Nanoparticles:

The methodology for synthesis of NaDyF4-NaGdF4 core-shell nanoparticles was adapted from previously described methods (Das et al, 2012). Briefly, dysprosium (III) chloride hexahydrate (1 mmol) was added to 1.5 mL oleic acid and 7.5 mL 1-octadecene in a three-necked 50 mL round bottom flask and stirred under vacuum at 120° C. for 45 min. The solution was brought back to room temperature, to which was added 2.5 mmol sodium hydroxide and 4 mmol ammonium fluoride in 10 mL methanol; the mixture was stirred for 1 h. Methanol was then removed at 80° C. The temperature was raised to 306° C. (~15° C./min) under argon and the solution was stirred vigorously for 1 h 15 min (Das et al, 2012). 1 mL of the cubic (α) NaGdF4 nanoparticles in 1-octadecene was injected into the solution and stirred for 15 min to form a core/shell nanostructure. The solution was cooled to room temperature. The nanoparticles were precipitated, washed with ethanol, centrifuged at 7000 g for 5 min, and finally dispersed in hexane.

Characterization of Nanoparticles:

Nanoparticles were characterized using Transmission electron microscopy (TEM) and X-ray diffraction. TEM images were acquired using a JEOL JEM-1400 microscope operating at 80 kV. The nanoparticle dispersion in hexane was drop-cast onto a formvar carbon film supported on a 300 mesh copper grid (3 mm in diameter) and allowed to dry in air at room temperature before imaging. The size distribution was obtained from averaging a minimum of 250 nanoparticles. X-ray diffraction patterns were collected using a Rigaku Miniflex diffractometer with Cr Kα radiation (λ=0.2290 nm, 30 kV, 15 mA) and a scan step size of 0.05° C. (2θ). 15 drops of the nanoparticle dispersion in hexane were added onto an indented zero-background sample holder and dried to get the diffraction patterns.

Figure 8:
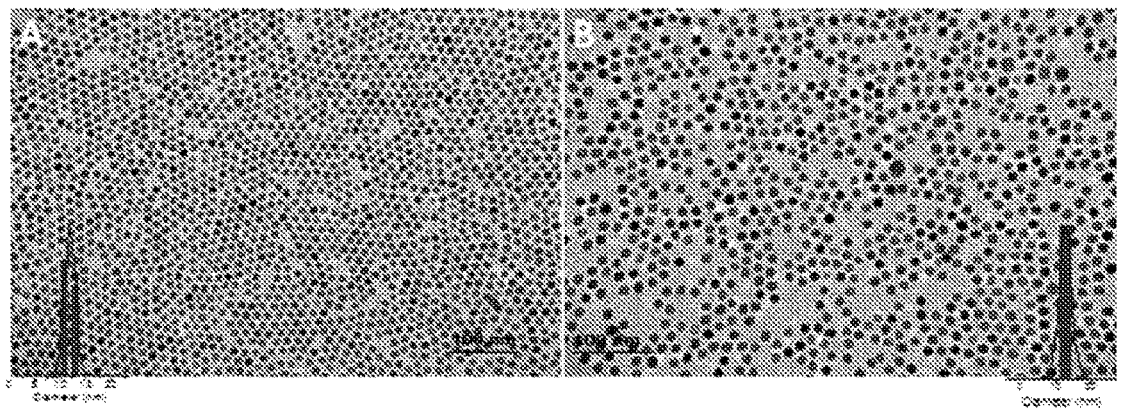
FIG. 8 shows Transmission Electron Microscopy (TEM) images of the NaDyF4-NaGdF4 core-shell nanoparticles from two different batches (FIGS. 8A and 8B); the histogram shows the size analysis of more than 250 nanoparticles.
Figure 9:
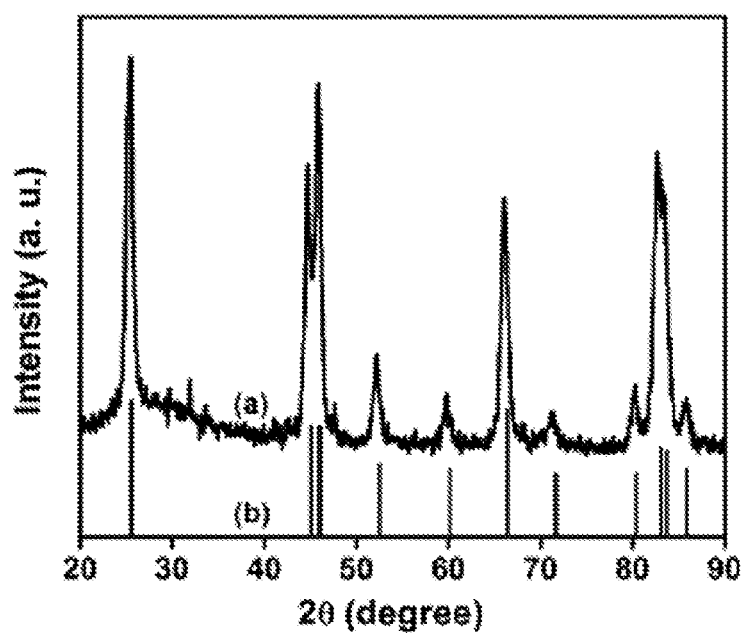
FIG. 9 is a X-ray diffraction pattern (line a) of NaDyF4-NaGdF4 core-shell nanoparticles indexed with their corresponding standard patterns (line b).

Results are shown in FIGS. 8 and 9. Transmission Electron Microscopy (TEM) images of the nanoparticles (FIG. 8) showed a fairly uniform and monodisperse size distribution (with <2% size dispersion) before and after the formation of the NaGdF4 shell around the core NaDyF4 nanoparticles. The respective average particle sizes obtained from analyzing over 250 nanoparticles in the TEM images were 11.83±0.01 and 12.53±0.10 nm. The shell was ~0.7 nm thick, comprising approximately 3 monolayers of NaGdF4. X-ray diffraction (XRD) patterns (FIG. 9) confirmed the hexagonal phase of NaDyF4/NaGdF4 core/shell nanoparticles. Thus, by controlling the reaction conditions, the nucleation-growth phases were controlled, resulting in the synthesis of fairly uniform NaDyF4/NaGdF4 core/shell nanoparticles.

Example 6: Bioconjugation of Anti-Tau sdAb to Nanoparticles

The NaDyF4-NaGdF4 core-shell nanoparticles produced and characterize in Example 5 were submitted to surface functionalization by phospholipids, followed by conjugation to the Tau15 sdAb (Example 3). Nanoparticles were prepared and conjugated to the anti-tau sdAb at the University of Victoria.

Surface Functionalization of NaDyF4/NaGdF4 Core/Shell Nanoparticles by Phospholipids:

NaDyF4/NaGdF4 core/shell nanoparticles were dispersed in 0.4 mL toluene at 7.0 mg/mL and added with a combination of DSPE-PEG-NH2, DSPE-PEG-COOH and DSPE-PEG-Biotin (Avanti Polar Lipids) in 0.8 mL chloroform in an appropriate weight ratio of DSPE-PEG to nanoparticle required for further steps of bioconjugation; the proportion of DSPE-PEG-NH2, DSPE-PEG-COOH and DSPE-PEG-Biotin in the combination will vary based on the desired sdAb:NP ratio (see below). 4 mL of DMSO was added slowly to the solution, which was then incubated on a shaker for 30 minutes at room temperature. Chloroform and toluene were removed completely by vaporization under vacuum. Deionized water was added to the colloidal solution in DMSO to total volume of 20 ml. DMSO was completely substituted with deionized water by three rounds of centrifugation in centrifugal filter tubes (Vivaspin Turbo 15, 100 kDa cutoff size). The final solution containing functionalized nanoparticles was filtered through 0.45 μm glass microfiber filter.

Binding Antibody and Streptavidin-Alexa 488 Conjugate with Nanoparticles:

NaDyF4/NaGdF4 core/shell nanoparticles were coated with 1,2-distearoyl-sn-glycero-3-phosphoethanolamine-N-[biotinyl(polyethylene glycol)-2000] (DSPE-PEG-biotin; Avanti Polar Lipids), 1,2-distearoyl-sn-glycero-3-phosphoethanolamine-N-[carboxyl(polyethylene glycol)-2000] (DSPE-PEG-COOH; Avanti Polar Lipids) and 1,2-distearoyl-sn-glycero-3-phosphoethanolamine-N-[methoxy (polyethylene glycol)-2000] (DSPE-mPEG; Avanti Polar Lipids) and dispersed in deionized water. 350 μL of the nanoparticle solution was diluted to 1 mL in deionized water and added with 50 μL of 2 mg/mL 1-[3-(dimethylamino)propyl]-3-ethylcarbodiimide methiodide (EDC.MeI) and 25 μL of 2 mg/mL N-hydroxysulfosuccinimide sodium salt (sulfo-NHS). The mixture was stirred for 30 min. 200 μL of 0.1 mg/mL anti-tau antibody (Tau15, Example 3) in 1× phosphate buffered saline was added to the solution and stirred for 2 h at room temperature. The solution was dialyzed overnight. 100 μL of 0.1 mg/mL streptavidin-Alexa 488 conjugate was added to the dialyzed solution and stirred for 0.5 h. The solution was centrifuged at 19000 g for 30 min and re-suspended in 10 mM phosphate buffered saline (pH 7.4). The same procedure was followed to bind the control antibody A20.1 to a separate identical batch of phospholipid-functionalized NaDyF4/NaGdF4 core/shell nanoparticles.

Binding NHS-Alexa 488 with Nanoparticles:

NaDyF4/NaGdF4 core/shell nanoparticles coated with 1,2-distearoyl-sn-glycero-3-phosphoethanolamine-N-[amino(polyethylene glycol)-2000] (DSPE-PEG-NH2; Avanti Polar Lipids) and DSPE-mPEG were dispersed in deionized water. 10 μL of 1 mg/mL NHS-Alexa 488 in anhydrous DMF was added to 1 mL of the nanoparticle dispersion and stirred overnight in the dark. The solution was centrifuged at 19000 g for 30 min and the pellet was re-suspended in 10 mM phosphate buffered saline.

Characterization of Antibody-Nanoparticle Conjugates:

The number of sdAbs per nanoparticle was derived using techniques as previously published (Pace & Schmid, 1997). UV absorption spectroscopy and Inductively Coupled Plasma Mass Spectrometry (ICP-MS) were used to determine the concentration of antibodies and Ln3+ ions, respectively, in a given nanoparticle-antibody conjugate sample. ICP-MS analysis was carried out using a Thermo X-Series II (X7) quadrupole ICP-MS. The aqueous dispersion of nanoparticles were digested in concentrated nitric acid at 135° C. in sealed Teflon vials for 3 days and diluted with ultrapure water before analysis. Calibration was done by analyzing serial dilutions of a mixed element synthetic standard containing a known amount of dysprosium. Each sample, standard and blank, was spiked with indium (to a concentration of ~7 ppb) as the internal standard to correct for signal drift and matrix effects. Accuracy was confirmed by analysis of a standard reference material.

The concentration of Dy3+ determined by ICP-MS in the stock solution was used to calculate the mass of NaDyF4 core employing the ratio:

$$\frac{M_{Dy}}{M_{NaDyF_4}} = 0.6215$$

The NaDyF4 core had a hexagonal closed pack crystal structure with a density of 5.1 g/cc. The mass of a nanoparticle was determined, making the assumption that the nanoparticle was a perfect sphere with radius r and volume $V=(4/3)\pi r^3$. Comparing the mass of the single nanoparticle and the total mass determined from ICP-MS, the total number of nanoparticles in the stock solution was determined. The nanoparticle-antibody conjugates showed typical UV absorption peaks at 280 nm. The molar absorption coefficient of the antibody at 280 nm, ε280 in $M^{-1}$ $cm^{-1}$, was calculated using the following equation:

$$\varepsilon_{280}=(5500\times\eta_{Trp})+(1490\times\eta_{Tyr})+(125\times\eta_{S-S})$$

where the numbers are the molar absorbance of tryptophan (Trp; 5500), tyrosine (Tyr; 1490) and cysteine (i.e., the disulphide bond, S—S; 125), $\eta_{Trp}$, $\eta_{Tyr}$ and $\eta_{S-S}$ are number of Trp, Tyr residues and disulphide bonds in the antibody, respectively. The concentration c of antibody was determined from the equation of Beer-Lambert law: Absorbance at 280 nm, $A=\varepsilon_{280}cl$, where l is the path length. UV absorption spectra were obtained in a PerkinElmer Lambda 1050 spectrometer using the photomultiplier tube detector in the UV range. Using the known molecular weights of antibodies, the average number of sdAb per nanoparticle in the stock solution was determined to be 4, 12 or 22.

Example 7: Immunocytochemistry in Hippocampal Co-Cultures

The sdAb-nanoparticle complex produced in Example 6 was utilized for in vitro testing in both live and fixed hippocampal neuronal co-cultures.

Hippocampal Co-Cultures:

Primary dissociated co-cultures of hippocampal neurons and glia were prepared from newborn (P0) Sprague Dawley rat pups (Charles River, USA) as previously described (Goda & Colicos, 2006). Co-cultures were plated at a density of $10^5$ cells/well in each well of a 24-well plate containing poly-D-lysine and laminin treated 12 mm round cover glass. Co-cultures were maintained in Basal Media Eagle supplemented with 4% fetal bovine serum (FBS), 2% B27, 10 mm HEPES, 1 mM sodium pyruvate, 100 U/ml penicillin, 100 µg/ml streptomycin and 2 mM L-glutamine. Two thirds of the growth medium was exchanged twice weekly.

Immunocytochemistry in Live Hippocampal Co-Cultures:

Anti-tau sdAb-NaDyF4-NaGdF4-Alexa488 or NaDyF4-NaGdF4-Alexa488 nanoparticles (4:1, 12:1, or 22:1 sdAb:NP) were directly added to the medium of hippocampal co-cultures at final concentrations of 1:5, 1:10, 1:20, or 1:50. Co-cultures were incubated with the nanoparticles overnight at 37° C., and imaging performed on an Olympus BX61W1 microscope with 40×0.8NA water-immersible lenses.

Immunocytochemistry in Fixed Hippocampal Co-Cultures:

Hippocampal neuron-glia co-cultures on 12 mm round cover glass (Fisher) were fixed for 20 min with 15% picric acid and 4% paraformaldehyde (PFA), then blocked and permeabilized with a 5% donkey serum, 5% goat serum, 2% BSA and 0.1% Triton X-100 PBS solution for 1 h at room temperature. Co-cultures were then incubated overnight in blocking solution containing 1:100 anti-tau sdAb-NaDyF4-NaGdF4-Alexa488 complex (4:1, 12:1, or 22:1 sdAb:NP), 1:100 NaDyF4-NaGdF4-Alexa488, or 1:200 rabbit anti-tau commercial antibody (Sigma Aldrich). Co-cultures treated with the rabbit anti-tau antibody were subsequently incubated with 1:2000 donkey anti-rabbit cy3 secondary antibody (Jackson Immunoresearch Labs) for 1 h. Imaging was initially performed on an Olympus BX61W1 microscope with 40×0.8NA water-immersible lenses. Images were taken with a Nikon D300 digital camera using Camera Control Pro 2 image capturing software (Nikon). Image processing was performed with Image J (NIH) and overlays in Photoshop CS6 (Adobe). Cover glasses were then mounted using Prolonged Gold+DAPI stain. Subsequently, images were taken using an ELYRA 3D super-resolution microscope.

Figure 10:
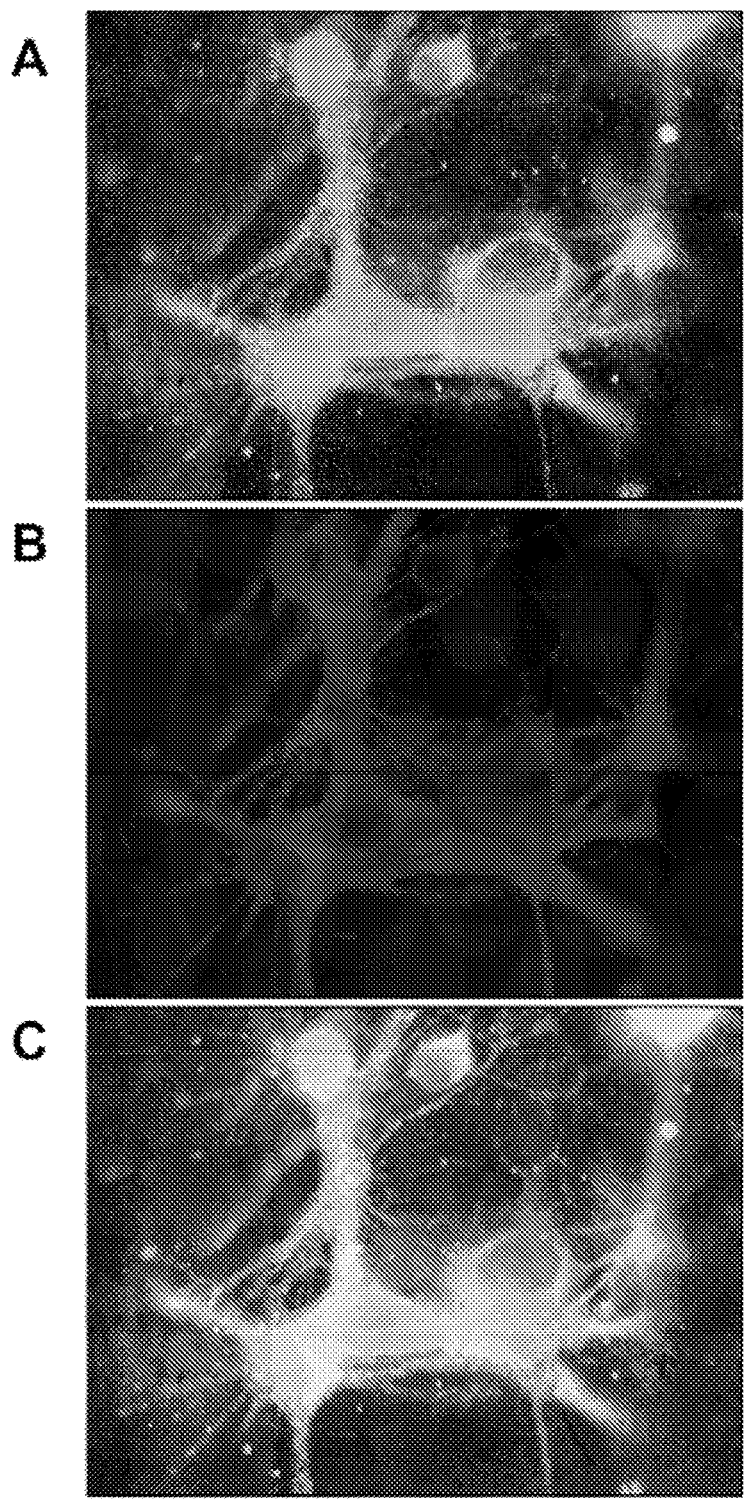
FIG. 10 is images of fixed hippocampal neurons labeled with anti-tau sdAb-NaDyF4-NaGdF4-Alexa488 (4:1 sdAb:NP ratio).
Figure 11:
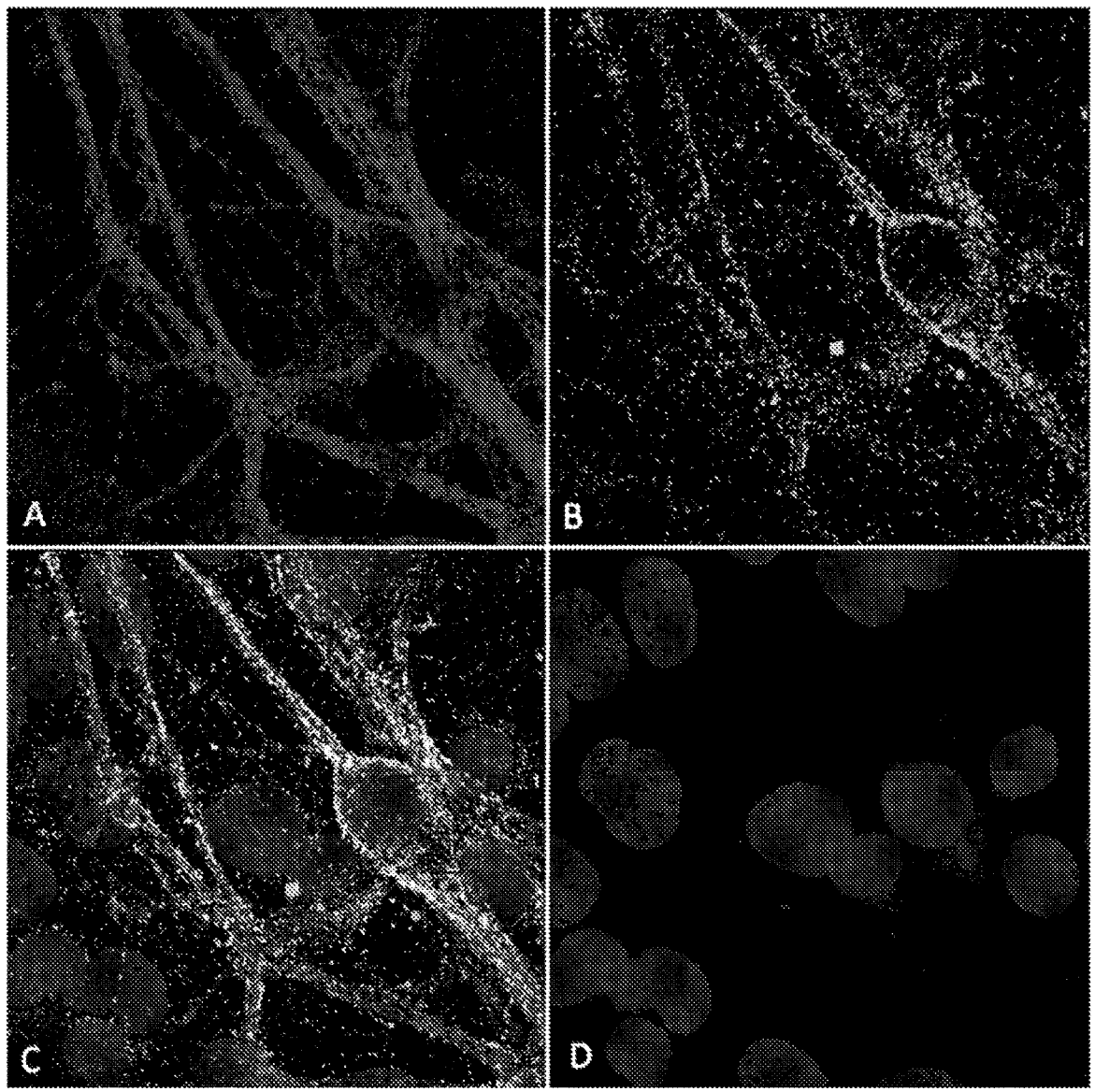
FIG. 11 shows super-resolution images of fixed hippocampal neurons labeled with 1:100 anti-tau sdAb-NaDyF4-NaGdF4-Alexa488 (4:1 sdAb:NP ratio) and co-cultured with 1:200 rabbit anti-tau commercial antibody treated with 1:2000 cy3 secondary antibody, using prolonged Gold+ DAPI stain. Fixed cell preparations with intraneuronal tau were labelled using commercial anti-tau antibody (FIG. 11A), anti-tau sdAb-NaDyF4-NaGdF4-Alexa488 (FIG. 11B), an overlay image (FIG. 11C) showing co-localization, and nuclear labeling with DAPI (FIG. 11D).
Figure 12:
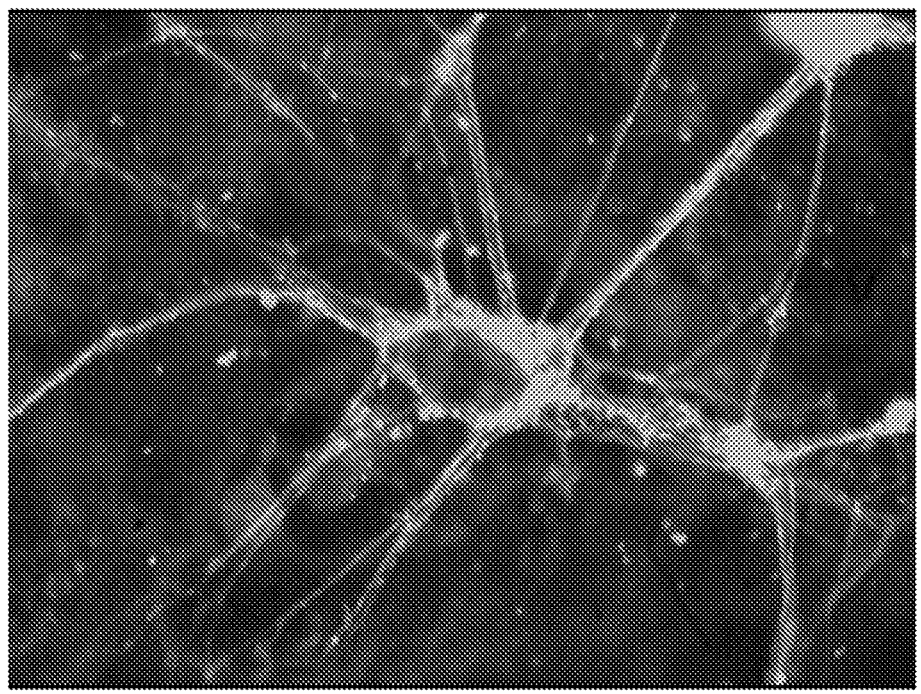
FIG. 12 is images of live hippocampal co-cultures labeled with anti-tau sdAb-NaDyF4-NaGdF4-Alexa488 (4:1 sdAb:NP ratio).
Figure 12:
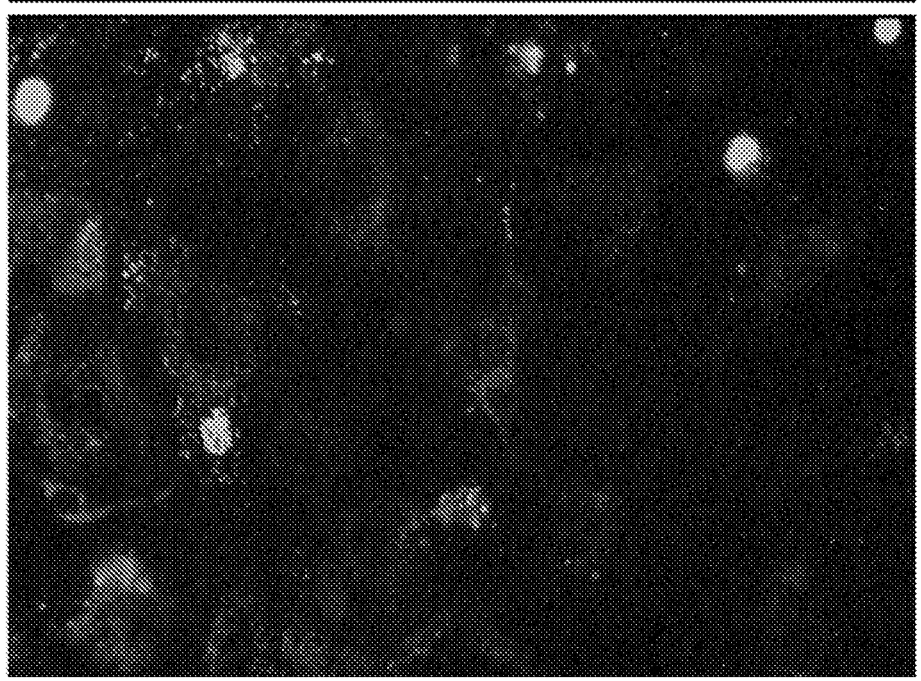

Results of labelling hippocampal co-cultures with anti-tau sdAb-NaDyF4-NaGdF4-Alexa488 nanoparticles and rabbit anti-tau commercial antibody are shown in FIG. 10 (A and B, respectively). The overlay of the 2 micrographs confirmed that both antibodies produce the same staining pattern in the fixed sample preparation (FIG. 10C). High resolution microscopy using the ELYRA imaging system clearly showed labeling of neuronal tau proteins with anti-tau sdAb-NaDyF4-NaGdF4-Alexa488 (FIG. 11). The anti-tau sdAb-NaDyF4-NaGdF4-Alexa488 complex also distinctly labeled neuronal tau proteins in live hippocampal co-culture preparations when added to the culture media for an overnight incubation at 37° C. (FIG. 12A). In contrast, NaDyF4-NaGdF4-Alexa488 alone, in absence of sdAb, failed to label any distinct structures (FIG. 12B).

The results showed that at the antibody-nanoparticle ratio of 4:1, anti-tau sdAb-NaDyF4-NaGdF4-Alexa488 was able to bind to intracellular tau, as demonstrated by specific neurite labeling at concentrations of 1:5 and 1:10 (experiments repeated twice). Indeed, the Alexa488 signal correlated well with the commercially available rabbit anti-tau/cy3. The presence of the anti-tau sdAb on the nanoparticles is essential for specific intracellular tau labeling, as evidenced by scattered non-specific background without intracellular signal when the cell culture is incubated with NaDyF4-NaGdF4-Alexa488 alone. The antibody-nanoparticle ratios of 12:1 and 22:1 failed to show any intracellular binding.

Example 8: Preparation, Expression and Purification of Dimeric Anti-Tau Antibodies Constructs comprising Tau15 (Example 2) fused to a human hinge region sequence or to a human antibody fragment crystallisable (Fc) to enhance its binding affinity. The PCR reaction mixture and PCR protocol utilized were as described in Baral et al (2013).

Briefly, a human IgG1 hinge sequence (ETSSPAEPK-SCDKTHTCPPCP; SEQ ID NO:17), a cmyc tag, and a $His_6$ tag were added to the C-terminal of the Tau15 $V_H$ sequence using primers:

```
BbsI2VHH:
                                    (SEQ ID NO: 18)
TATGAAGACAC.CAGGCCCAGGTAAAGCTGGAGGAGTCT
and HING1FOR:
                                    (SEQ ID NO: 19)
CAGTTGTTCGGATCCTGGGCACGGTGGGCATGTGTG.
``` to produce the dimeric hinge Tau15 construct (DH-Tau15; SEQ ID NO:20).

To create the Fc-fusion construct (Fc-Tau15), the Tau 15 VH was re-amplified by PCR using the following primers to add the EcoRI site for cloning into pTT5-Fc1 cassette:

```
hFc5:
           (EcoRI site is underlined; SEQ ID NO: 21)
5'TCTAGCGAATTCGCCACCATGGAGTTTGGGCTGAGCTGGGTTTTCCT TGTTGCTATTTTGAAAGGTGTCCAGTGT-3'
and BamH1FR4:
                                    (SEQ ID NO: 22)
5'-GGGGTACCTGTCATCCACGGACCAGCTGA-3'.
```

The sequence of the full Fc-Tau15 fusion construct is given in SEQ ID NO:23.

The amplified PCR products were purified with a QIAquick PCR purification kit (Qiagen), digested with BbsI and BamH1 for the hinge dimer or EcoR1 and BstEII for Fc fusion (New England Biolabs, Canada), and re-purified using the same kit.

The hinge dimer PCR products were cloned into the pSJF2H expression vector between BbsI and BamHI restriction enzyme sites. The final construct further included an OmpA leader sequence, for secretion of sdAb proteins to the periplasmic space of *E. coli*. The Fc PCR products were cloned in pTT5 vector between EcoRI and BstEII restriction enzyme sites to replace an existing camelid $V_HH$ in the pTT5-Fc fusion cassette (Durocher, 2002).

The dimeric hinge Tau15 was expressed and purified as described in Example 3. A mammalian cell line was transfected with the Fc-Tau15 construct, and the $V_H$-Fc fusion was expressed and purified as previously described in Tom et al (2008). Briefly, 100 µg of Fc-Tau15 plasmid DNA was used to transiently transfect HEK-293-6E cells. Expressed Fc-Tau15 fusion proteins were harvested from the cell culture supernatant and purified by protein A affinity chromatography.

Figure 13:
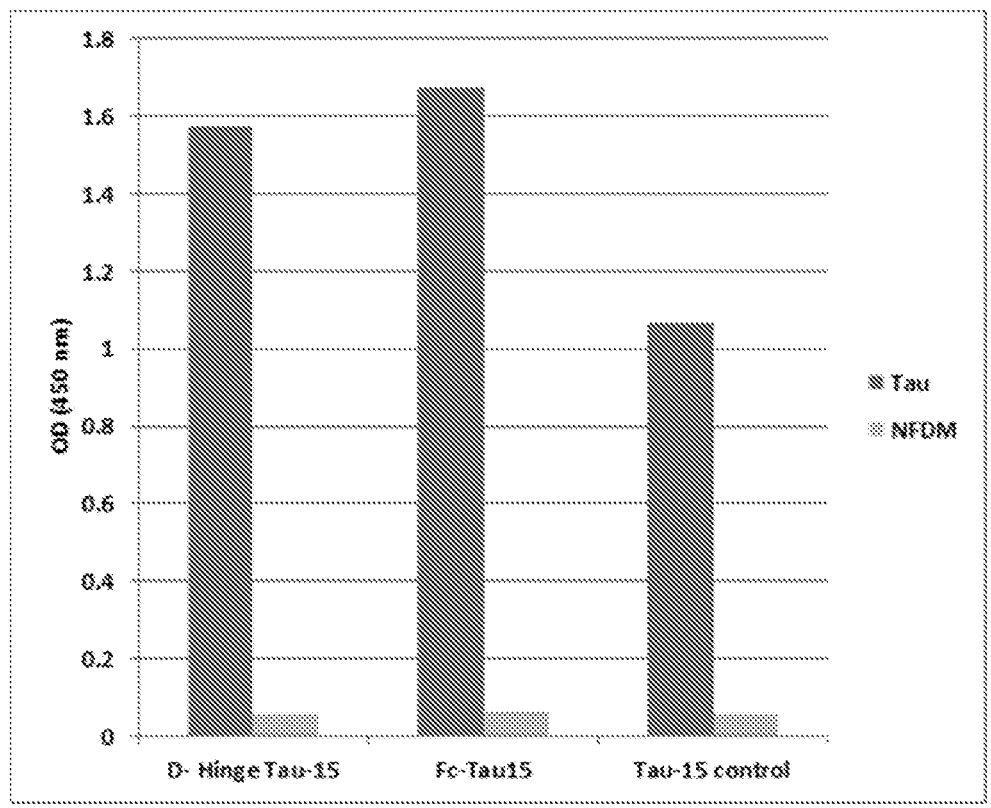
FIG. 13 is a bar graph showing results of protein ELISA for Tau15 (control), dimeric human hinge Tau15 (DH-Tau15), and Tau15-Fc fusion (Fc-Tau15). Both dimeric versions of Tau15 show strong binding to Tau-441 (Tau) and no binding to the negative control (non-fat dry milk; NFDM).

Protein ELISA was performed for DH-Tau15 and Fc-Tau15 as described in Example 3, except that bound DH- Tau15 was detected using a rabbit anti-6His-HRP conjugate, while bound Tau-15 was detected using a protein A-HRP conjugate. The results of protein ELISA are shown in FIG. 13, where strong binding signals for DH-Tau15 and Fc-Tau15 were observed.

Example 9: Biophysical Characterization of Dimeric Anti-Tau sdAb

The DH-Tau15 and Fc-Tau15 constructs expressed and purified in Example 8 were characterized using size exclusion chromatography and surface plasmon resonance analysis.

Figure 14A:
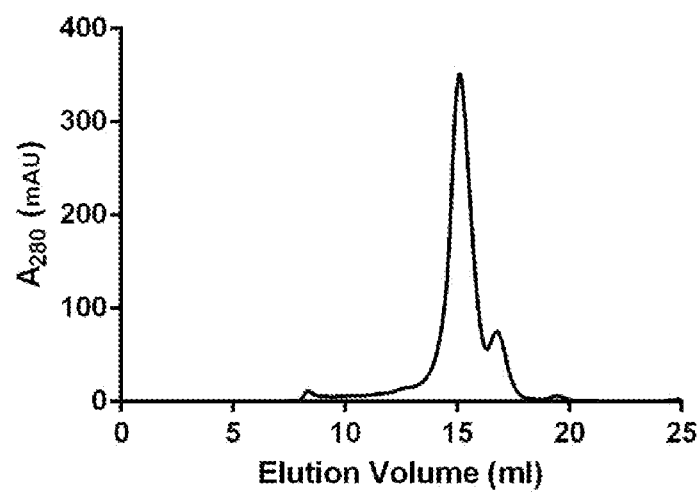
FIG. 14 shows size-exclusion chromatography profiles of purified DH-Tau15 (FIG. 14A) and Fc-Tau15 (FIG. 14B), with Tau15 shown in FIG. 14C for reference. The Fc-Tau15 and DH-Tau15 formed dimers, though the DH-Tau15 showed a smaller peak corresponding to a small fraction of the construct that remained in monomeric form.
Figure 14B:
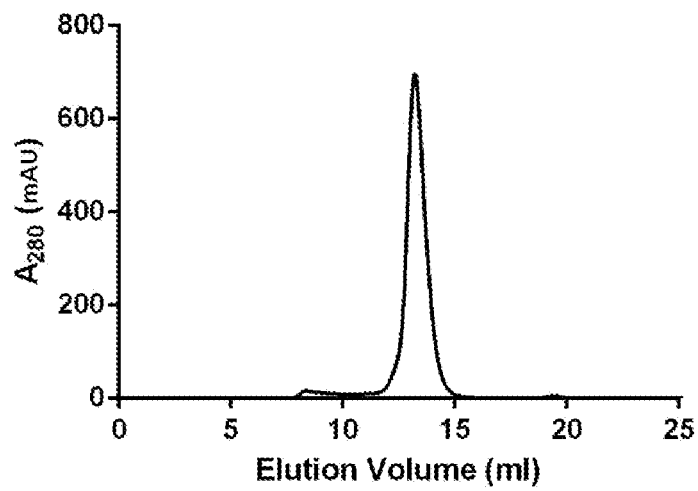
Figure 14C:
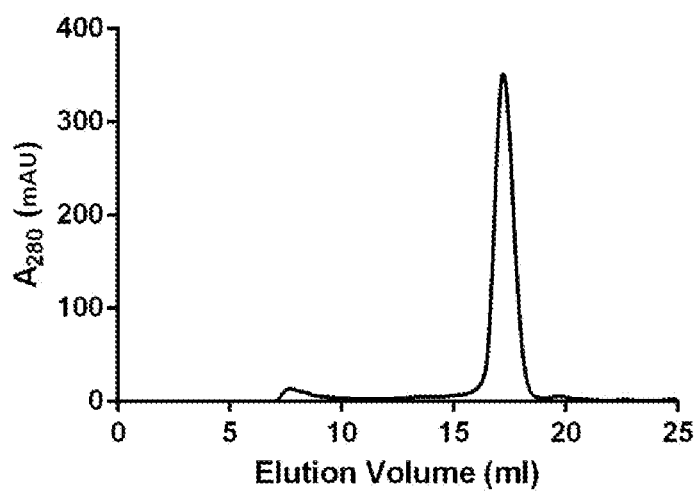

Size Exclusion Chromatography:

Size exclusion chromatography for the DH-Tau15 and Fc-Tau15 were performed as described in Example 4. The SEC analysis suggested that the antibody constructs were non-aggregating, based on the elution volume compared to standards (FIG. 14). However, a small peak (at the elution volume expected to be monomeric VH, which did not form the dimer) was observed in the dimeric hinge chromatogram.

Surface Plasmon Resonance (SPR):

All binding assays for DH-Tau15 and Fc-Tau15 were carried out at 25° C. on a Biacore™ 3000 instrument (GE Healthcare). For binding analysis, approximately 5000 resonance units (RUs) of Tau-441 (Sigma Aldrich) diluted in 10 mM acetate buffer pH 4.5 were immobilized on a CM5 Series S sensor chip (GE Healthcare) using an amine coupling kit (GE Healthcare). DH-Tau15, Fc-Tau15 and monomeric Tau15 (Examples 3 and 8) were injected over immobilized Tau-441 at a concentration of 1-5 nM in duplicate for determining the off rates of monomer and dimers. The running buffer for all SPR experiments was HBS-EP+ (10 mM HEPES, 150 mM NaCl, 3 mM EDTA, pH 7.4, 0.05% surfactant P20; GE Healthcare). The antibodies were injected at 20 μL/min for 2 min with a dissociation time of 30 min. Data was analyzed using the Biacore 3000 BIAevaluations software Version 4.1.

Figure 15:
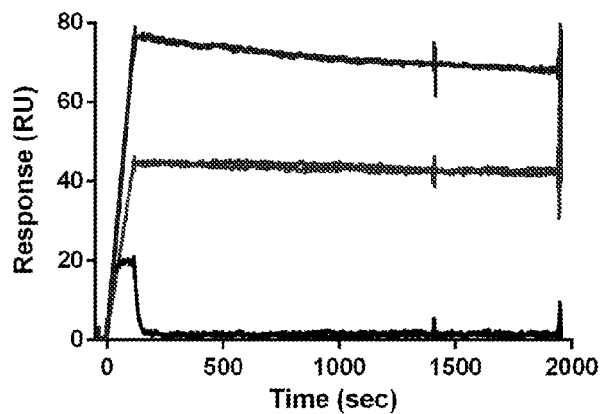
FIG. 15 shows results of SPR analysis of the binding of the Tau15 constructs to tau. An overlay of the sensorgrams for Fc-Tau15 (top line), DH-Tau15 (middle line), and Tau15 monomer (bottom line) is shown.

Results of SPR analysis are shown in FIG. 15 and Table 1. As shown in Example 4, monomeric Tau15 showed binding to tau with fast on and off rates. However, DH-Tau15 and Fc-Tau15 showed very slow off rate—approximately 1000 times slower.

TABLE 1

Off rates of anti-tau sdAb for Tau-441.

| | $k_d$ (1/s) |
|---|---|
| Fc-Tau15 | $6.73 \times 10^{-05}$ |
| Fc-Tau15 | $7.02 \times 10^{-05}$ |
| DH-Tau15 | $4.27 \times 10^{-05}$ |
| DH-Tau15 | $3.45 \times 10^{-05}$ |
| Tau15 | $6.32 \times 10^{-02}$ |
| Tau15 | $6.67 \times 10^{-02}$ |

Example 10: Anti-Tau sdAb for In Vivo Imaging

The sdAb-nanoparticle complex produced in Example 6 was utilized for in vivo imaging in rats with induced head trauma. A schematic showing the experimental protocol is shown in FIG. 16A.

Figure 16A:
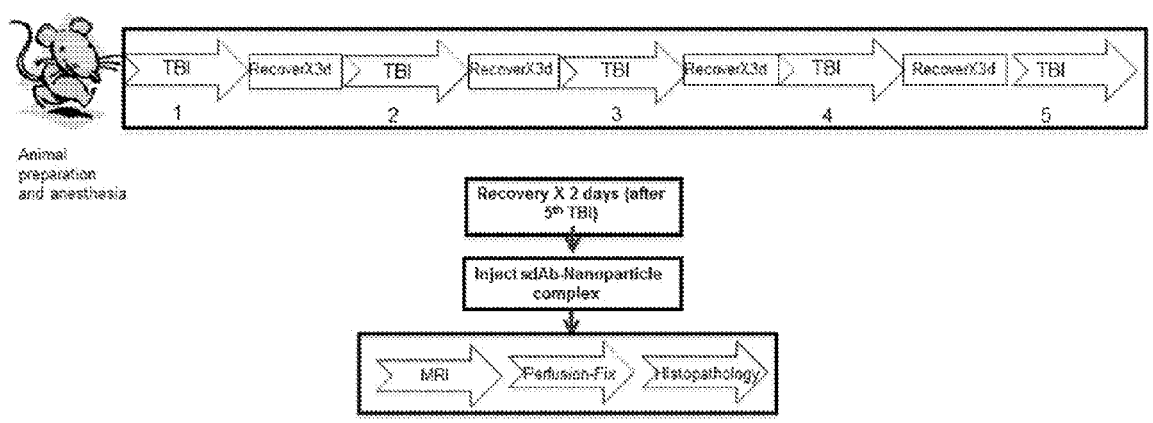
FIG. 16A is a schematic showing the protocol for mild repetitive TBI experiments.

Mild Repetitive TBI Experiments:

A total of 6 animals were studied, TBI group (n=4) received five impacts (see Induction of head trauma, below) 3 days apart (FIG. 16A). Two days following the last impact, rats underwent MR imaging before and 15 min after tail-vein injection of anti-tau sdAb-naDyF4-NaGdF4-Alexa488 (Example 6; (500 μL total following reconstitution in saline solution). T1 and T2 images were acquired. Non TBI control animals (n=2) were anesthetized in same manner as TBI animals, but did not receive trauma (procedure repeated 5 times at 3 day intervals). Forty-eight hours after the last anesthesia, animals were imaged before and after the injection of the sdAb-nanoparticle complex.

Induction of Head Trauma.

The scalp of the anesthetized animal was shaved, a midline incision made, and the periosteum covering the vertex reflected. A metallic disc/helmet was placed centrally on the skull vault between the coronal and lambdoid sutures. The rat was placed securely in prone position on a foam bed of known spring constant. The lower end of the Plexiglas tube was positioned directly above the helmet. Mild TBI injury was induced using 101.23 g-30 cm weight-height interface (a modified Marmarou technique). Rebound impact was prevented by sliding the foam bed containing the animal away from the tube immediately following impact.

MR Imaging:

A 9.4T/21 cm horizontal bore magnet (Magnex, UK) with a Biospec console (Bruker, Germany) was used for MR imaging. The volume radiofrequency coil (3 cm diameter×3 cm length) was applied for signal transmission and reception. After placing an animal in the magnet under maintenance anesthesia, axial slices were positioned within the sample. T1, T2 and T2* were measured using, as appropriate: (1) inversion recovery (IR) spin echo: TR/TE=4 s/8 ms, 20 IR times from 50 ms to 5 sec; (2) multi-echo spin echo (ME SE): TR=7.5 sec, first echo 4 ms, 128 echoes; (3) multi-echo gradient echo (GE): TR=300 ms, flip angle 30°, 128 echoes with first echo 4 ms. For all sequences, the following parameters were used: field of view (FOV)=3×3 cm, matrix 128×128, bandwidth 50 kHz and slice thickness of 1 mm. T1, T2 and T2* values of the samples were calculated using a single exponential fitting of the signal from the regions of interest (ImageJ, NIH USA). MR acquisitions were performed prior to the injection of anti-tau sdAb-NaDyF4-NaGdF4 nanoparticle complex, as well as 15 and 30 minutes following the injection of the agent.

TABLE 2

Specific MRI MSME MR parameters for T2W and T1W sequences.

| | T2W sequence | T1W sequence |
|---|---|---|
| FOV | 25.6 × 25.6 mm | 25.6 × 25.6 mm |
| MX | 256 × 256 | 256 × 256 |
| | 20 slices × 1.00 mm | 20 slices × 1.00 mm |
| TR | 2000 ms | 750 ms |
| TE | 30 ms | 7.5 ms |
| NA | 2 | 10 |

Histopathology and Immunohistochemistry:

After the completion of MR imaging studies, the animals were euthanized, perfusion was fixed with formaldehyde, and the brain processed for histopathology. Hematoxylin and eosin staining of coronal brain sections, at the level of the cortex, hippocampi and striatum were acquired for qualitative assessment of morphological changes associated with mild repetitive TBI, such as sub-arachnoid hemorrhage, petechial hemorrhage, and inflammation.

Figure 16B:
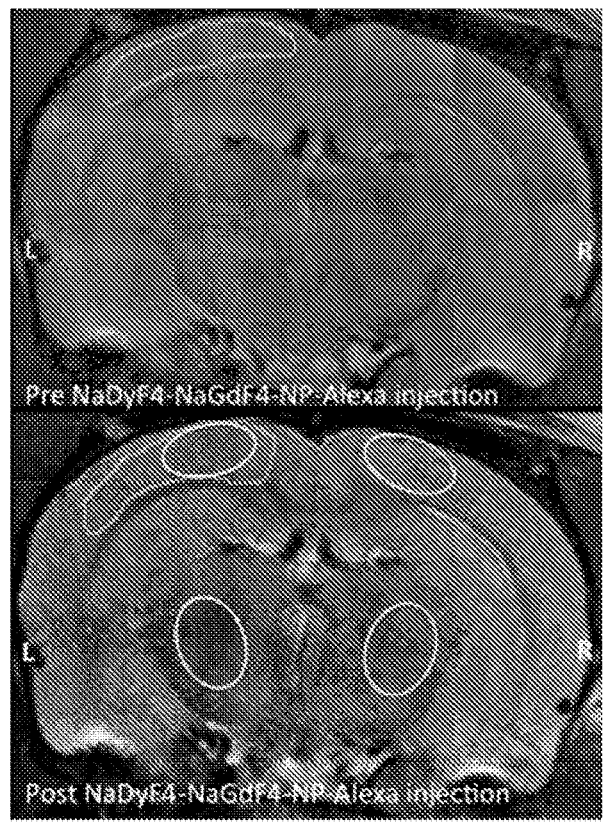
FIG. 16B shows a representative T2 weighted MR image of an animal pre- and post-injection of the anti-tau sdAb-naDyF4-NaGdF4-Alexa488 nanoparticle complex (top and bottom, respectively). The regions of interest, freehand and ovals, represent MR signal intensity changes before and after the injection of the complex, comparing bilateral cortices and thalami.
Figure 16C:
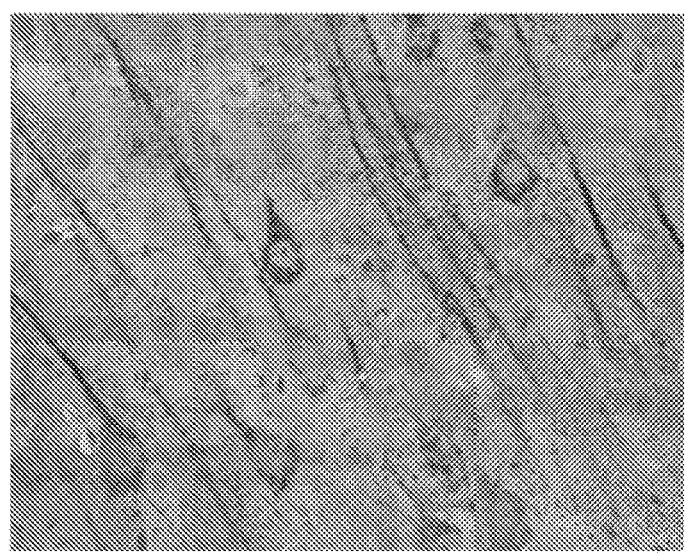
FIG. 16C is a histopathology image of the same animal, left cortex, staining positive for tau.

Representative results are shown FIG. 16. MR imaging showed imaging signal changes with T2 hypointensity observed in two rats, mainly in the left cortices, hippocampi, and thalamus. There were some non-specific signal changes in the remaining two animals, with mild tau staining in one and no staining the other. Tau histopathology showed positive staining for tau mainly in the cortex of the affected rats, with imaging correlation. Staining for tau showed immunoreactivity of tau and confirmed deposition of neurofibrillary tangles or hyperphosphorylated tau. Although imaging changes were noted in thalamus in three out of four animals, the area only showed weakly positive staining for tau. Control animals did not show any of the changes noted for rats with TBI.

The results show that the anti-tau antibodies and anti-tau antibody conjugates of the present invention are useful for imaging in vivo. The findings are unique and demonstrate for the first time that tau is able to be visualized using a novel tau specific sdAb-nanoparticle complex and MR imaging. This establishes the present visualization approach as a non-invasive, non radio-active imaging biomarker for mild repetitive TBI, which presently does not exist.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

SEQUENCES

| SEQ ID NO: | SEQUENCE | DESCRIPTION |
|---|---|---|
| 1 | GFTFSNFA | CDR1 Tau15 |
| 2 | IDNDGGRT | CDR2 Tau15 |
| 3 | AAMNLATRKWEL | CDR3 Tau15 |
| 4 | GFTGDHYA | CDR1 Tau81 |
| 5 | IYSYSPNT | CDR2 Tau81 |
| 6 | AADLEVAEYYAY | CDR3 Tau81 |
| 7 | QVKLEESGGGLVQPGGSLRLSCAASGFTFSNFAMTWVRQSPGKGL EWVSAIDNDGGRTSYSDSVKGRFTISRDNAKNTLYLQMNSLKPED TAMYYCAAMNLATRKWELWGQGTQVTVSS | Tau15 |
| 8 | QVQLVESGGGLVQPGGSLKLSCAASGFTGDHYAMSWVRQAPGKGL EWVSTIYSYSPNTYYVDSVKDRFTISLDNAKNTLYLQMNSLKPED TAVYYCAADLEVAEYYAYWGQGTQVTVSS | Tau81 |
| 9 | GCCCAGCCGGCCATGGCCSMKGTGCAGCTGGTGGAKTCTGGGGGA | MJ1 primer |
| 10 | GCCCAGCCGGCCATGGCCCAGGTAAAGCTGGAGGAGTCTGGGGGA | MJ2 primer |
| 11 | GCCCAGCCGGCCATGGCCCAGGCTCAGGTACAGCTGGTGGAGTCT | MJ3 primer |
| 12 | CGCCATCAAGGTACCAGTTGA | CH2 primer |
| 13 | GGGGTACCTGTCATCCACGGACCAGCTGA | CH2b3 primer |
| 14 | CATGTGTAGACTCGCGGCCCAGCCGGCCATGGCC | MJ7 primer |
| 15 | CATGTGTAGATTCCTGGCCGGCCTGGCCTGAGGAGACGGTGACCTGG | MJ8 primer |
| 16 | AEPISCDKTHTCPPCP | Human hinge sequence |
| 17 | ETSSPAEPKSCDKTHTCPPCP | Human IgG1 hinge sequence |
| 18 | TATGAAGACAC•CAGGCCCAGGTAAAGCTGGAGGAGTCT | BbsI2VHH primer |
| 19 | CAGTTGTTCGGATCCTGGGCACGGTGGGCATGTGTG | HING1FOR primer |
| 20 | QVKLEESGGGLVQPGGSLRLSCAASGFTFSNFAMTWVRQSPGKGL EWVSAIDNDGGRTSYSDSVKGRFTISRDNAKNTLYLQMNSLKPED TAMYYCAAMNLATRKWELWGQGTQVTVSSETSSPAEPKSCDKTHT CPPCPGSEQKLISEEDLNHHHHHH | DH-Tau15 |
| 21 | TCTAGCGAATTCGCCACCATGGAGTTTGGGCTGAGCTGGGTTTTC CTTGTTGCTATTTTGAAAGGTGTCCAGTGT | hFc5 primer |
| 22 | GGGGTACCTGTCATCCACGGACCAGCTGA | BamH1FR4 primer |

-continued

SEQUENCES

| SEQ ID NO: | SEQUENCE | DESCRIPTION |
|---|---|---|
| 23 | QVKLEESGGGLVQPGGSLRLSCAASGFTFSNFAMTWVRQSPGKGL EWVSAIDNDGGRTSYSDSVKGRFTISRDNAKNTLYLQMNSLKPED TAMYYCAAMNLATRKWELWGQGTQVTVSSAEPISCDKTHTCPPCP APELLGGPSVFLFPPKPKDTLMISRTPEVTCVVVDVSHEDPEVKF NWYVDGVEVHNAKTKPREEQYNSTYRVVSVLTVLHQDWLNGKEYK CKVSNKALPAPIEKTISKAKGQPREPQVYTLPPSRDELTKNQVSL TCLVKGFYPSDIAVEWESNGQPENNYKTTPPVLDSDGSFFLYSKL TVDKSRWQQGNVFSCSVMHEGLHNHYTQKSLSLSPG | Fc-Tau15 |

REFERENCES

All patents, patent applications and publications referred to herein and throughout the application are listed below.

Arbabi-Ghahroudi, M. Desmyter A, Wyns L, Hamers R., and Muyldermans S (1997) Selection and identification of single domain antibody fragments from camel heavy-chain antibodies, FEBS Lett 414, 521-526

Arbabi-Ghahroudi M., MacKenzie R., and Tanha J. (2009b) Methods Mol. Biol. 525, 187-216.

Avila, J., et al. Tau in neurodegenerative diseases: tau phosphorylation and assembly. Neurotox Res. 6, 477-482 (2004)

Ballatore C, Lee V M, Trojanowski J Q. Tau-mediated neurodegeneration in Alzheimer's disease and related disorders. Nat Rev Neurosci. 2007 September; 8(9):663-72.

Baral N. T., Mackenzie, R., Arbabi-Ghahroudi, M. (2013) Single domain antibodies and their utility. Current protocol Immunology 103, Unit 2.17.1-57.

Bell A., Wang Z. J., Arbabi-Ghahroudi M., Chang T. A., Durocher Y., Trojahn U., Baardsnes J., Jaramillo M. L., Li S., Baral T. N., O'Connor-McCourt M., Mackenzie R., and Zhang J. (2010) Cancer Lett. 289, 81-90.

Bigler E D, Maxwell W L. Neuropathology of mild traumatic brain injury: relationship to neuroimaging findings. Brain Imaging Behay. 2012 June; 6(2):108-36.

Chothia C., and Lesk A. M. (1987) J. Mol. Biol. 196, 901-917.

Corrigan J D, Selassie A W, Orman J A. The epidemiology of traumatic brain injury. J Head Trauma Rehabil 2010 March-April; 25(2):72-80

Davies J., and L. Riechmann, Affinity improvement of single antibody VH domains: residues in all three hypervariable regions affect antigen binding. Immunotechnology 2 (1996) 169-179

G. K. Das, N. J. J. Johnson, J. Cramen, B. Blasiak, P. Latta, B. Tomanek, and F. C. J. M. van Veggel; NaDyF4 Nanoparticle: NaDyF4 nanoparticles: a Highly Efficient T2 Contrast Agent for Ultra-High Field Magnetic Resonance Imaging J. Phys. Chem. Lett. 2012, 3, 524-529

DeKosky S T, Ikonomovic M D, Gandy S. Traumatic brain injury—football, warfare, and long-term effects. N Engl J Med 2010 Sep. 30; 363(14):1293-1296.

De Kruif, J., and Logtenberg, T. (1996) J. Biol. Chem. 271, 7630-7634.

Dumoulin, M., Conrath, K., Van Meirhaighe, A., Meersman, F., Heremans, K., Frenken, L. G., Muyldermans, S., Wyns, L., and Matagne, A. (2002) Protein Sci 11, 500-515.

Durocher, Y., S. Perret, et al. (2002). "High-level and high-throughput recombinant protein production by transient transfection of suspension-growing human 293-EBNA1 cells." Nucleic Acids Res 30(2): E9.

Eierud, C., et al. Neuroimaging after mild traumatic brain injury: Review and meta-analysis. Neuroimage Clin. 4, 283-294 (2014).

Eisenberg, D., Schwarz, E., Komaromy, M., and Wall, R. (1984) J. Mol. Biol. 179, 125-142

Fenner, L., Widmer, A. F., Goy, G., Rudin, S., and Frei, R. (2008) J. Clin. Microbiol. 46, 328-330.

Fodero-Tavoletti, M. T., et al. 18F-THK523: a novel in vivo tau imaging ligand for Alzheimer's disease. Brain 134, 1089-1100 (2011).

Goda, Y. & Colicos, M. A. Photoconductive stimulation of neurons cultured on silicon wafers. Nat. Protoc. 1, 461-467 (2006)

Goldstein L E, Fischer A M, Tagge C A, Zhang X-L, Velisek L et al. Chronic Traumatic Encephalopathy in Blast-Exposed Military Veterans and a Blast Neurotrauma Mouse Model. Sci Transl Med 134(4), 134ra60 (2012)

Grundke-Iqbal I, Iqbal K, Quinlan M, Tung Y C, Zaidi M S, Wisniewski H M (1986a) Microtubule-associated protein tau. A component of Alzheimer paired helical filaments. J Biol Chem 261, 6084-6089.

Grundke-Iqbal I, Iqbal K, Tung Y C, Quinlan M, Wisniewski H M, Binder L I (1986b) Abnormal phosphorylation of the microtubule-associated protein tau (tau) in Alzheimer cytoskeletal pathology. Proc Natl Acad Sci USA 83, 4913-4917.

Hamers-Casterman, C., Atarhouch, T., Muyldermans, S., Robinson, G., Hamers, C., Songa, E. B., Bendahman, N., and Hamers, R. (1993) Nature 363, 446-448.

Hirokawa, N., Funakoshi, T., Sato-Harada, R. & Kanai, Y. Selective stabilization of tau in axons and microtubule-associated protein 2C in cell bodies and dendrites contributes to polarized localization of cytoskeletal proteins in mature neurons. J. Cell Biol. 132, 667-679 (1996)

Hussack G., Hirama T., Ding W., MacKenzie R., and Tanha J. (2011) PLoS ONE 6, e28218.

Iqbal U., Trojahn U., Albaghdadi H., Zhang J., O'Connor M., Stanimirovic D., Tomanek B., Sutherland G., and Abulrob A. (2010) Br. J. Pharmacol. 160, 1016-1028.

Jaffee M S, Meyer K S. A brief overview of traumatic brain injury (TBI) and post-traumatic stress disorder (PTSD) within the Department of Defense. Clin Neuropsychol 2009 November; 23(8):1291-1298.

Jeganathan, S., von Bergen, M., Mandelkow, E. M. & Mandelkow, E. The natively unfolded character of tau and its aggregation to Alzheimer-like paired helical filaments. Biochemistry 47, 10526-10539 (2008).

Jespers, L., Schon, O., Famm, K., and Winter, G. (2004) Nat. Biotechnol. 22, 1161-1165.

Johnson V E, Stewart W, Smith D H. Traumatic brain injury and amyloid-beta pathology: a link to Alzheimer's disease? Nat Rev Neurosci 2010 May; 11(5):361-70

Johnson, N. J. J., Korinek, A., Dong, C. & van Veggel, F. C. J. M. Self-Focusing by Ostwald Ripening: A Strategy for Layer-by-Layer Epitaxial Growth on Upconverting Nanocrystals. Journal of the American Chemical Society 134, 11068-11071 (2012)

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991; 147:1709-19.

Kane M J, Angoa-Perez M, Briggs D I, Viano D C, Kreipke C W, Kuhn D M. A mouse model of human repetitive mild traumatic brain injury. J Neurosci Methods 2011 Sep. 12.

Kim, D. Y., Kandalaft, H., Ding, W., Ryan, S., van Fassen, H., Hirama, T., Foote, S. J., MacKenzie, R., and Tanha, J. (2012) PEDS advance access Aug. 30, 2012, 1-9.

Klimo P, Jr, Ragel B T. Introduction: military neurosurgery, past and present. Neurosurg Focus 2010 May; 28(5): Introduction Lefranc, M.-P. et al., (2003) Dev. Comp. Immunol., 27, 55-77.

Li S, Zheng W, Kuolee R, Hirama T, Henry M, Makvandi-Nejad S, Fjallman T, Chen W, Zhang J. Pentabody-mediated antigen delivery induces antigen-specific mucosal immune response. Mol Immunol 2009; 46:1718-26.

Marshall S, Bayley M, McCullagh S, Velikonja D, Berrigan L. Clinical practice guidelines for mild traumatic brain injury and persistent symptoms. Can Fam Physician. 2012 March; 58(3):257-67, e128-40

McKee A C, Cantu R C, Nowinski C J, Hedley-Whyte E T, Gavett B E et al. Chronic traumatic encephalopathy in athletes: progressive tauopathy after repetitive head injury. J Neuropathol Exp Neurol 2009 July; 68(7):709-735

Merritt, E. A., and Hol, W. G. (1995) Curr. Opin. Struct. Biol. 5, 165-171.

Musher, D. M., Manhas, A., Jain, P., Nuila, F., Waqar, A., Logan, N., Marino, B., Graviss, E. A. (2007) J. Clin. Microbiol. 45, 2737-2739.

Neely, A., et al. Ultrasensitive and highly selective detection of Alzheimer's disease biomarker using two-photon Rayleigh scattering properties of gold nanoparticle. ACS Nano 3, 2834-2840 (2009)

Nicaise M, Valeio-Lepiniec M, Minard P, Desmadril M. (2004) Affinity transfer by CDR grafting on a nonimmunoglobulin scaffold. Protein Sci. 13(7): 1882-1891.

Nuttall, S. D., Krishnan, U. V., Doughty, L., Pearson, K., Ryan, M. T., Hoogenraad, N. J., Hattarki, M., Carmichael, J. A., Irving, R. A., and Hudson, P. J. (2003) Eur. J. Biochem. 270, 3543-3554.

Pace, C. N. & Schmid, F. X. How to determine the molar absorbance coefficient of a protein. Protein Structure: A Practical Approach 253-259 (1997)

Park E, Bell J D, Baker A J. Traumatic brain injury: can the consequences be stopped? CMAJ 2008 Apr. 22; 178(9): 1163-1170

Pickett W, Ardern C, Brison R J. A population-based study of potential brain injuries requiring emergency care. CMAJ 2001 Aug. 7; 165(3):288-292.

Planche, T., Aghaizu, A., Holliman, R., Riley, P., Poloniecki, J., Breathnach, A., and Krishna, S. (2008) Lancet Infect. Dis. 8, 777-784.

Rüssmann, H., Panthel, K., Bader, R. C., Schmitt, C., and Schaumann, R. (2007) Eur. J. Clin. Microbiol. Infect. Dis. 26, 115-119.

Selenica, M. L., et al. Epitope analysis following active immunization with tau proteins reveals immunogens implicated in tau pathogenesis. J. Neuroinflammation 11, 152-014-0152-0 (2014).

Tanha, J., Dubuc, G., Hirama, T., Narang, S. A. & MacKenzie, C. R. Selection by phage display of llama conventional V(H) fragments with heavy chain antibody V(H)H properties. J. Immunol. Methods 263, 97-109 (2002).

To, R., Hirama, T., Arbabi-Ghahroudi, M., MacKenzie, R., Wang, P., Xu, P., Ni, F., and Tanha, J. (2005) J. Biol. Chem. 280, 41395-41403.

Tom R., Bisson L., Durocher Y. (2008) Culture of HEK293-EBNA1 Cells for Production of Recombinant Proteins. CSH Protocols, 3, 1-4.

Turgeon, D. K., Novicki, T. J., Quick, J., Carlson, L., Miller, P., Ulness, B., Cent, A., Ashley, R., Larson, A., Coyle, M., Limaye, A. P., Cookson, B. T., and Fritsche, T. R. (2003) J. Clin. Microbiol. 41, 667-670.

Vagnozzi R, Signoretti S, Tavazzi B, Cimatti M, Amorini A M, Donzelli S, et al. (2005) Hypothesis of the postconcussive vulnerable brain: experimental evidence of its metabolic occurrence. Neurosurgery, 57(1):164-71.

Vagnozzi R, Tavazzi B, Signoretti S, Amorini A M, Belli A, Cimatti M, et al. Temporal window of metabolic brain vulnerability to concussions: mitochondrial-related impairment—part I. Neurosurgery 2007 August; 61(2): 379-88; discussion 388-9

Van Den Heuvel C., Thornton E., Vink R. (2007) Traumatic brain injury and Alzheimer's disease: a review. Progress in Brain Research, Vol. 161, Chapter 21, 303-316.

Weber J T. Experimental models of repetitive brain injuries. Prog Brain Res 2007; 161:253-261.

Zetterberg, H., Smith, D. H. & Blennow, K. Biomarkers of mild traumatic brain injury in cerebrospinal fluid and blood. Nat. Rev. Neurol. 9, 201-210 (2013)

Zhang, J., Li, Q., Nguyen, T.-D., Tremblay, T.-L., Stone, E., To, R., Kelly, J., and MacKenzie, C. R. (2004a) J. Mol. Biol. 341, 161-169.

Zhang, J., Tanha, J., Hirama, T., Khiew, N. H., To, R., Tong-Sevinc, H., Stone, E., Brisson, J. R., and MacKenzie, C. R. (2004b) J. Mol. Biol. 335, 49-56.

Zhu et al., Immunology and Cell Biology (2010) 88:667-675.

European Patent No. 519596

European Patent No. 626390

U.S. Pat. No. 5,693,761

U.S. Pat. No. 5,766,886

U.S. Pat. No. 5,821,123

U.S. Pat. No. 5,859,205

U.S. Pat. No. 5,869,619

U.S. Pat. No. 6,054,297

U.S. Pat. No. 6,180,370

WO 95/04069

WO/2004/076670

WO2003/046560

The invention claimed is:

1. An isolated or purified antibody or fragment thereof, comprising
   a complementarity determining region (CDR) 1 sequence of GFTFSNFA (SEQ ID NO:1) or GFTGDHYA (SEQ ID NO:4);
   a CDR2 sequence of IDNDGGRT (SEQ ID NO:2) or IYSYSPNT (SEQ ID NO:5);
   a CDR3 sequence of AAMNLATRKWEL (SEQ ID NO:3) or AADLEVAEYYAY (SEQ ID NO:6); and
   valine at position 42, glycine at position 49, leucine at position 50, and tryptophan at position 52 of the framework (IMGT numbering),
   wherein the antibody or fragment thereof specifically binds to Tau.

2. The isolated or purified antibody or fragment thereof of claim 1, wherein the antibody comprises
   a CDR1 sequence of GFTFSNFA (SEQ ID NO:1), a CDR2 sequence of IDNDGGRT (SEQ ID NO:2), and a CDR3 sequence of AAMNLATRKWEL (SEQ ID NO:3); or
   a CDR1 sequence of GFTGDHYA (SEQ ID NO:4), a CDR2 sequence of IYSYSPNT (SEQ ID NO:5), and a CDR3 sequence of AADLEVAEYYAY (SEQ ID NO:6).

3. The isolated or purified antibody or fragment thereof of claim 1, comprising a sequence selected from the group consisting of:

(SEQ ID NO: 7)
QVKLEESGGGLVQPGGSLRLSCAASGFTFSNFAMTWVRQSPGKGLEWVS

AIDNDGGRTSYSDSVKGRFTISRDNAKNTLYLQMNSLKPEDTAMYYCAA

MNLATRKWELWGQGTQVTVSS;

(SEQ ID NO: 8)
QVQLVESGGGLVQPGGSLKLSCAASGFTGDHYAMSWVRQAPGKGLEWVS

TIYSYSPNTYYVDSVKDRFTISLDNAKNTLYLQMNSLKPEDTAVYYCAA

DLEVAEYYAYWGQGTQVTVSS;

and
   a sequence at least 90% identical thereto.

4. The isolated or purified antibody or fragment thereof of claim 1, wherein the antibody is a single-domain antibody (sdAb).

5. The isolated or purified antibody or fragment thereof of claim 4, wherein the sdAb is of camelid origin.

6. The isolated or purified antibody or fragment thereof of claim 1, wherein the antibody or fragment thereof is in a multivalent display format.

7. The isolated or purified antibody or fragment thereof of claim 6, wherein the antibody or fragment thereof is linked to a Fc, $C_{H1}$ domain, $C_{H2}$ domain, $C_{H3}$ domain, a hinge region, or a combination thereof.

8. A nucleic acid molecule encoding the isolated or purified antibody or fragment thereof of claim 1.

9. A vector comprising the nucleic acid molecule of claim 8.

10. The isolated or purified antibody or fragment thereof of claim 1, wherein the antibody or fragment thereof is immobilized onto a surface or is linked to a cargo molecule.

11. The isolated or purified antibody or fragment thereof of claim 10, wherein the cargo molecule is a detectable agent, or a liposomes or nanocarriers loaded with a detectable agent.

12. The isolated or purified antibody or fragment thereof of claim 11, wherein the detectable label is a radioisotope, a paramagnetic label, a fluorophore, a Near Infra-Red (NIR) fluorochrome, a dye, an echogenic microbubble, or a superparamagnetic nanoparticle, optionally wherein the nanoparticle has a size of about 10 to about 50 nm.

13. The isolated or purified antibody or fragment thereof of claim 12, wherein the nanoparticle is a NaDyF4-NaGdF4 core-shell nanoparticle, a silica-coated ferrous oxide, gold nanoparticle, β-NaYF$_4$:Yb,Gd,Tm, gadolinium nanoparticle, or a solid lipid nanoparticle.

14. The isolated or purified antibody or fragment thereof of claim 12, wherein there are about 4 to about 22 antibodies or fragment thereof conjugated to the surface of the nanoparticle.

15. An in vitro method of detecting tau, comprising
  a) contacting a tissue sample with one or more than one isolated or purified antibody or fragment thereof of claim 1 linked to a detectable agent; and
  b) detecting the detectable agent linked to the antibody or fragment thereof bound to tau in the tissue sample, optionally wherein the step of detecting (step b) is performed using optical imaging, immunohistochemistry, molecular diagnostic imaging, ELISA, or imaging mass spectrometry.

16. The method of claim 15, wherein the tissue sample is a brain tissue sample from a human or animal subject.

17. An in vivo method of detecting tau expression in a subject, comprising:
  a) administering one or more than one isolated or purified antibody or fragment thereof of claim 1 linked to a detectable agent to the subject; and
  b) detecting the detectable agent linked to the antibody or fragment thereof bound to tau, optionally wherein the step of detecting (step b) is performed using magnetic resonance imaging (MRI).

18. The method of claim 17, wherein the detectable agent is a superparamagnetic nanoparticle, optionally wherein the nanoparticle has a size of about 10 to about 50 nm, or optionally wherein the nanoparticle is a NaDyF4-NaGdF4 core-shell nanoparticle.

19. The method of claim 18, wherein the antibody or fragment thereof is SEQ ID NO:7.

20. The method of claim 18, wherein there are about 4, 12, or 22 antibodies or fragments thereof conjugated to the surface of the nanoparticle.

* * * * *

SEQUENCE LISTING

```
<160> NUMBER OF SEQ ID NOS: 23

<210> SEQ ID NO 1
<211> LENGTH: 8
<212> TYPE: PRT
<213> ORGANISM: Artificial Sequence
<220> FEATURE:
<223> OTHER INFORMATION: CDR1 Tau15

<400> SEQUENCE: 1

Gly Phe Thr Phe Ser Asn Phe Ala
1               5

<210> SEQ ID NO 2
<211> LENGTH: 8
<212> TYPE: PRT
<213> ORGANISM: Artificial Sequence
<220> FEATURE:
<223> OTHER INFORMATION: CDR2 Tau15

<400> SEQUENCE: 2

Ile Asp Asn Asp Gly Gly Arg Thr
1               5

<210> SEQ ID NO 3
<211> LENGTH: 12
<212> TYPE: PRT
<213> ORGANISM: Artificial Sequence
<220> FEATURE:
<223> OTHER INFORMATION: CDR3 Tau15

<400> SEQUENCE: 3

Ala Ala Met Asn Leu Ala Thr Arg Lys Trp Glu Leu
1               5                   10

<210> SEQ ID NO 4
<211> LENGTH: 8
<212> TYPE: PRT
<213> ORGANISM: Artificial Sequence
<220> FEATURE:
<223> OTHER INFORMATION: CDR1 Tau81

<400> SEQUENCE: 4

Gly Phe Thr Gly Asp His Tyr Ala
1               5

<210> SEQ ID NO 5
<211> LENGTH: 8
<212> TYPE: PRT
<213> ORGANISM: Artificial Sequence
<220> FEATURE:
<223> OTHER INFORMATION: CDR2 Tau81

<400> SEQUENCE: 5

Ile Tyr Ser Tyr Ser Pro Asn Thr
1               5

<210> SEQ ID NO 6
<211> LENGTH: 12
<212> TYPE: PRT
<213> ORGANISM: Artificial Sequence
<220> FEATURE:
<223> OTHER INFORMATION: CDR3 Tau81

<400> SEQUENCE: 6

Ala Ala Asp Leu Glu Val Ala Glu Tyr Tyr Ala Tyr
1               5                   10
```

<210> SEQ ID NO 7
<211> LENGTH: 119
<212> TYPE: PRT
<213> ORGANISM: Artificial Sequence
<220> FEATURE:
<223> OTHER INFORMATION: Tau15

<400> SEQUENCE: 7

Gln Val Lys Leu Glu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Ala Met Thr Trp Val Arg Gln Ser Pro Gly Lys Gly Leu Glu Trp Val
        35                  40                  45

Ser Ala Ile Asp Asn Asp Gly Arg Thr Ser Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Met Asn Leu Ala Thr Arg Lys Trp Glu Leu Trp Gly Gln Gly
            100                 105                 110

Thr Gln Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: Tau81

<400> SEQUENCE: 8

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Gly Asp His Tyr
            20                  25                  30

Ala Met Ser Trp Val Arg Gln Ala Pro Gly Lys Gly Leu Glu Trp Val
        35                  40                  45

Ser Thr Ile Tyr Ser Tyr Ser Pro Asn Thr Tyr Tyr Val Asp Ser Val
    50                  55                  60

Lys Asp Arg Phe Thr Ile Ser Leu Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Asp Leu Glu Val Ala Glu Tyr Tyr Ala Tyr Trp Gly Gln Gly
            100                 105                 110

Thr Gln Val Thr Val Ser Ser
        115

<210> SEQ ID NO 9
<211> LENGTH: 45
<212> TYPE: DNA
<213> ORGANISM: Artificial Sequence
<220> FEATURE:
<223> OTHER INFORMATION: MJ1 primer

<400> SEQUENCE: 9
gcccagccgg ccatggccsm kgtgcagctg gtggaktctg gggga            45

<210> SEQ ID NO 10
<211> LENGTH: 45
<212> TYPE: DNA
<213> ORGANISM: Artificial Sequence
<220> FEATURE:
<223> OTHER INFORMATION: MJ2 primer

<400> SEQUENCE: 10
gcccagccgg ccatggccca ggtaaagctg gaggagtctg gggga            45

<210> SEQ ID NO 11
<211> LENGTH: 45
<212> TYPE: DNA
<213> ORGANISM: Artificial Sequence
<220> FEATURE:
<223> OTHER INFORMATION: MJ3 primer

<400> SEQUENCE: 11
gcccagccgg ccatggccca ggctcaggta cagctggtgg agtct            45

<210> SEQ ID NO 12
<211> LENGTH: 21
<212> TYPE: DNA
<213> ORGANISM: Artificial Sequence
<220> FEATURE:
<223> OTHER INFORMATION: CH2 primer

<400> SEQUENCE: 12
cgccatcaag gtaccagttg a                                      21

<210> SEQ ID NO 13
<211> LENGTH: 29
<212> TYPE: DNA
<213> ORGANISM: Artificial Sequence
<220> FEATURE:
<223> OTHER INFORMATION: CH2b3 primer

<400> SEQUENCE: 13
ggggtacctg tcatccacgg accagctga                              29

<210> SEQ ID NO 14
<211> LENGTH: 34
<212> TYPE: DNA
<213> ORGANISM: Artificial Sequence
<220> FEATURE:
<223> OTHER INFORMATION: MJ7 primer

<400> SEQUENCE: 14
catgtgtaga ctcgcggccc agccggccat ggcc                        34

<210> SEQ ID NO 15
<211> LENGTH: 47
<212> TYPE: DNA
<213> ORGANISM: Artificial Sequence
<220> FEATURE:
<223> OTHER INFORMATION: MJ8 primer

<400> SEQUENCE: 15
catgtgtaga ttcctggccg gcctggcctg aggagacggt gacctgg          47

<210> SEQ ID NO 16
<211> LENGTH: 16
<212> TYPE: PRT
<213> ORGANISM: Artificial Sequence
<220> FEATURE:
<223> OTHER INFORMATION: Human hinge sequence

<400> SEQUENCE: 16

Ala Glu Pro Ile Ser Cys Asp Lys Thr His Thr Cys Pro Cys Pro
1               5                   10                  15

<210> SEQ ID NO 17
<211> LENGTH: 21
<212> TYPE: PRT
<213> ORGANISM: Artificial Sequence
<220> FEATURE:
<223> OTHER INFORMATION: Human IgG1 hinge sequence

<400> SEQUENCE: 17

Glu Thr Ser Ser Pro Ala Glu Pro Lys Ser Cys Asp Lys Thr His Thr
1               5                   10                  15

Cys Pro Pro Cys Pro
            20

<210> SEQ ID NO 18
<211> LENGTH: 38
<212> TYPE: DNA
<213> ORGANISM: Artificial Sequence
<220> FEATURE:
<223> OTHER INFORMATION: Bbsl2VHH primer

<400> SEQUENCE: 18
tatgaagaca ccaggcccag gtaaagctgg aggagtct                              38

<210> SEQ ID NO 19
<211> LENGTH: 36
<212> TYPE: DNA
<213> ORGANISM: Artificial Sequence
<220> FEATURE:
<223> OTHER INFORMATION: HING1FOR primer

<400> SEQUENCE: 19
cagttgttcg gatcctgggc acggtgggca tgtgtg                                36

<210> SEQ ID NO 20
<211> LENGTH: 159
<212> TYPE: PRT
<213> ORGANISM: Artificial Sequence
<220> FEATURE:
<223> OTHER INFORMATION: DH-Tau15

<400> SEQUENCE: 20

Gln Val Lys Leu Glu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Ala Met Thr Trp Val Arg Gln Ser Pro Gly Lys Gly Leu Glu Trp Val
        35                  40                  45

Ser Ala Ile Asp Asn Asp Gly Gly Arg Thr Ser Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Met Asn Leu Ala Thr Arg Lys Trp Glu Leu Trp Gly Gln Gly
            100                 105                 110

```
Thr Gln Val Thr Val Ser Ser Glu Thr Ser Ser Pro Ala Glu Pro Lys
            115                 120                 125

Ser Cys Asp Lys Thr His Thr Cys Pro Pro Cys Pro Gly Ser Glu Gln
    130                 135                 140

Lys Leu Ile Ser Glu Glu Asp Leu Asn His His His His His His
145                 150                 155

<210> SEQ ID NO 21
<211> LENGTH: 75
<212> TYPE: DNA
<213> ORGANISM: Artificial Sequence
<220> FEATURE:
<223> OTHER INFORMATION: hFc5 primer

<400> SEQUENCE: 21
tctagcgaat cgccaccat ggagtttggg ctgagctggg ttttccttgt tgctattttg    60
aaaggtgtcc agtgt                                                   75

<210> SEQ ID NO 22
<211> LENGTH: 29
<212> TYPE: DNA
<213> ORGANISM: Artificial Sequence
<220> FEATURE:
<223> OTHER INFORMATION: BamH1FR4 primer

<400> SEQUENCE: 22
ggggtacctg tcatccacgg accagctga                                    29

<210> SEQ ID NO 23
<211> LENGTH: 351
<212> TYPE: PRT
<213> ORGANISM: Artificial Sequence
<220> FEATURE:
<223> OTHER INFORMATION: Fc-Tau15

<400> SEQUENCE: 23

Gln Val Lys Leu Glu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Ala Met Thr Trp Val Arg Gln Ser Pro Gly Lys Gly Leu Glu Trp Val
        35                  40                  45

Ser Ala Ile Asp Asn Asp Gly Arg Thr Ser Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Met Asn Leu Ala Thr Arg Lys Trp Glu Leu Trp Gly Gln Gly
            100                 105                 110

Thr Gln Val Thr Val Ser Ser Ala Glu Pro Ile Ser Cys Asp Lys Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
```

-continued

|  | 180 |  |  |  | 185 |  |  |  | 190 |  |  |
|---|---|---|---|---|---|---|---|---|---|---|---|
| Lys | Thr | Lys | Pro | Arg | Glu | Glu | Gln | Tyr | Asn | Ser | Thr | Tyr | Arg | Val | Val |
|  |  | 195 |  |  |  |  | 200 |  |  |  | 205 |  |  |  |  |

Lys Thr Lys Pro Arg Glu Glu Gln Tyr Asn Ser Thr Tyr Arg Val Val
        195                 200             205

Ser Val Leu Thr Val Leu His Gln Asp Trp Leu Asn Gly Lys Glu Tyr
        210             215             220

Lys Cys Lys Val Ser Asn Lys Ala Leu Pro Ala Pro Ile Glu Lys Thr
225         230             235                 240

Ile Ser Lys Ala Lys Gly Gln Pro Arg Glu Pro Gln Val Tyr Thr Leu
            245             250             255

Pro Pro Ser Arg Asp Glu Leu Thr Lys Asn Gln Val Ser Leu Thr Cys
            260             265             270

Leu Val Lys Gly Phe Tyr Pro Ser Asp Ile Ala Val Glu Trp Glu Ser
            275             280             285

Asn Gly Gln Pro Glu Asn Asn Tyr Lys Thr Thr Pro Pro Val Leu Asp
        290             295             300

Ser Asp Gly Ser Phe Phe Leu Tyr Ser Lys Leu Thr Val Asp Lys Ser
305             310             315             320

Arg Trp Gln Gln Gly Asn Val Phe Ser Cys Ser Val Met His Glu Gly
                325             330             335

Leu His Asn His Tyr Thr Gln Lys Ser Leu Ser Leu Ser Pro Gly
            340             345             350